United States Patent
Arnold et al.

(10) Patent No.: US 10,477,859 B2
(45) Date of Patent: Nov. 19, 2019

(54) PLANT EMBRYO STORAGE AND MANIPULATION

(71) Applicant: PIONEER HI-BRED INTERNATIONAL, INC., Johnston, IA (US)

(72) Inventors: Randal Arnold, Ankeny, IA (US); Matthew Paul Cope, Johnston, IA (US); Justin Andrew Schares, Ames, IA (US); Yue Yun, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 1 day.

(21) Appl. No.: 15/507,032

(22) PCT Filed: Jun. 4, 2015

(86) PCT No.: PCT/US2015/034129
§ 371 (c)(1),
(2) Date: Feb. 27, 2017

(87) PCT Pub. No.: WO2016/032587
PCT Pub. Date: Mar. 3, 2016

(65) Prior Publication Data
US 2017/0273297 A1    Sep. 28, 2017

Related U.S. Application Data

(63) Continuation-in-part of application No. 14/473,183, filed on Aug. 29, 2014, now Pat. No. 9,078,427.

(51) Int. Cl.
*A01N 3/00* (2006.01)
*A01H 1/04* (2006.01)
*A01H 4/00* (2006.01)

(52) U.S. Cl.
CPC .............. *A01N 3/00* (2013.01); *A01H 1/04* (2013.01); *A01H 4/00* (2013.01); *A01H 4/001* (2013.01)

(58) Field of Classification Search
CPC ... A01N 3/00; A01H 1/04; A01H 4/00; A01H 4/001; A01H 1/005; A01H 1/001; A01H 1/008; A01C 1/025; A01G 22/00; C12Q 1/6806; C12Q 1/6895; C12N 5/04; C12N 5/0025
USPC ............................. 435/420; 47/57.6
See application file for complete search history.

(56) References Cited

U.S. PATENT DOCUMENTS

| | | | |
|---|---|---|---|
| 5,138,793 A * | 8/1992 | Florin | A01H 4/00 435/1.1 |
| 5,565,335 A | 10/1996 | Capon et al. | |
| 5,943,821 A | 8/1999 | Ducos et al. | |
| 6,145,247 A | 11/2000 | McKinnis | |
| 6,180,405 B1 | 1/2001 | Aitken-Christie et al. | |
| 6,200,808 B1 * | 3/2001 | Simmonds | A01H 4/00 435/242 |
| 6,455,312 B1 | 9/2002 | Gray et al. | |
| 6,627,441 B1 | 9/2003 | Attree | |
| 6,677,154 B2 | 1/2004 | Gielis et al. | |
| 6,689,609 B1 | 2/2004 | Fan et al. | |
| 6,695,765 B1 | 2/2004 | Beebe et al. | |
| 6,905,843 B1 | 6/2005 | Endo et al. | |
| 7,326,826 B2 | 2/2008 | Gray et al. | |
| 7,665,243 B2 | 2/2010 | Nehra et al. | |
| 7,915,006 B2 | 3/2011 | Cope et al. | |
| 7,935,529 B2 | 5/2011 | Davis et al. | |
| 8,119,342 B2 | 2/2012 | Van Dun | |
| 8,216,840 B2 | 7/2012 | Jamruszka | |
| 8,216,841 B2 | 7/2012 | Nehra et al. | |
| 8,313,946 B2 | 11/2012 | Becwar et al. | |
| 8,321,191 B2 | 11/2012 | Jones, III | |
| 8,404,930 B2 | 3/2013 | Wu et al. | |
| 8,452,460 B2 | 5/2013 | Aidun | |
| 8,465,707 B2 * | 6/2013 | Curran | B01F 13/0071 422/501 |
| 8,535,877 B2 | 9/2013 | Cope et al. | |
| 8,859,846 B2 | 10/2014 | Barton et al. | |
| 8,865,971 B2 | 10/2014 | Zhao et al. | |
| 9,404,930 B2 | 8/2016 | Grabulovski et al. | |
| 9,416,394 B2 | 8/2016 | Rapier et al. | |
| 2002/0174454 A1 | 11/2002 | Lopez-Molina et al. | |
| 2002/0188965 A1 | 12/2002 | Zhao | |
| 2003/0005489 A1 | 1/2003 | Gray et al. | |
| 2005/0050592 A1 | 3/2005 | Gray et al. | |
| 2005/0186655 A1 | 8/2005 | Endo et al. | |

(Continued)

FOREIGN PATENT DOCUMENTS

| | | | |
|---|---|---|---|
| AU | 703582 B2 | 3/1999 | |
| AU | 750133 B2 | 2/2000 | |

(Continued)

OTHER PUBLICATIONS

Sharma et al. In vitro conservation of Bacopa monnieri (L.) using mineral oil, Plant Cell Tiss. Organ Cult. (2012) 11 pp. (Year: 2012).*

(Continued)

*Primary Examiner* — June Hwu

(57) ABSTRACT

Methods for obtaining genetic material from plant embryos while preserving their viability are provided. In the methods, preservation of viability may be maintained by suspending the embryos in an aqueous solution surrounded by an oil matrix. Genetic material may be obtained from an aliquot of the aqueous solution and may be used directly for molecular analysis, or whole genome amplification may be performed prior to molecular analysis.

12 Claims, 17 Drawing Sheets

(56) References Cited

U.S. PATENT DOCUMENTS

| | | |
|---|---|---|
| 2005/0202573 A1 | 9/2005 | Koyota |
| 2005/0246790 A1 | 11/2005 | Gray et al. |
| 2006/0041959 A1 | 2/2006 | Hooykaas et al. |
| 2007/0204366 A1 | 8/2007 | Deppermann |
| 2008/0216191 A1 | 4/2008 | Barton et al. |
| 2009/0215060 A1 | 8/2009 | Depperman et al. |
| 2010/0167376 A1 | 7/2010 | Hogan et al. |
| 2010/0184152 A1 | 7/2010 | Sandler et al. |
| 2012/0131849 A1* | 5/2012 | Asada ............... A01C 1/02 47/58.1 SE |
| 2012/0202289 A1 | 8/2012 | Aidun |
| 2012/0276634 A1 | 11/2012 | Clark et al. |
| 2013/0065762 A1 | 3/2013 | Stoller et al. |
| 2015/0191771 A1 | 7/2015 | Bullock et al. |

FOREIGN PATENT DOCUMENTS

| | | |
|---|---|---|
| AU | 765886 B2 | 3/2000 |
| CA | 2296362 A1 | 11/1999 |
| CA | 2276003 A1 | 12/1999 |
| CA | 2322438 A1 | 12/1999 |
| CA | 2125410 C | 3/2000 |
| CN | 101165174 A | 4/2008 |
| CN | 102246959 A | 11/2011 |
| CN | 103657769 A | 3/2014 |
| GB | 2091534 A | 8/1982 |
| ID | 201302434 A | 6/2013 |
| WO | 1989/05575 A1 | 6/1989 |
| WO | 1995/014373 A1 | 6/1995 |
| WO | 1998/37173 A2 | 8/1998 |
| WO | 2002/085014 A | 10/2002 |
| WO | 2005/000471 A1 | 1/2005 |
| WO | 2005/030988 A | 4/2005 |
| WO | 2007/103786 A2 | 9/2007 |
| WO | 2011/019863 A1 | 2/2011 |
| WO | 2011/119763 A1 | 9/2011 |
| WO | 2012/011091 A2 | 1/2012 |
| WO | 2013/119962 A1 | 8/2013 |
| WO | 2013/182646 A | 12/2013 |
| WO | 2014/071271 A1 | 5/2014 |
| WO | 2014/195199 A1 | 12/2014 |
| WO | 2015/104358 A1 | 7/2015 |

OTHER PUBLICATIONS

Antoine-Michard, et al.; "Spontaneous versus colchicine-induced chromosome doubling in maize anther culture", Plant Cell, Tissue and Organ Culture, (1997) 48:203-297.

Horn, et al. "Non-Destructive RAPD Genetic Diagnosis of Micropspore-Derived *Brassica* Embryos", Plant Molecular Biology Reporter, (1992) 10(3):286-293.

Kato, Maize Genetics Cooperation Newsletter (1997) pp. 36-37.

King, et al.;"Perfluorocarbons and Cell Culture", Biotechnology, (1989) 7:1037-1042.

McKentley, et al.; "Agrobacterium-mediated transformation of peanut (*Arachis hypogaea* L.) embryo axes and the development of transgenic plants"; Plant Cell Reports (1995) 14:699-703.

The International Search Report and Written Opinion of the International Searching Authority for PCT/US2015/039449, dated Oct. 7, 2015.

Nadarajan, et al.; "Optimization of cryopreservation for sterculia cordata zygotic embryos using vitrification techniques"; Journal of Tropical Forest Science (2007) 19(2):79-85.

Nagano, et al.; "Effects of temperature and moisture content of the substrate during storage on embryo development and germination in seeds of Musa velutina Wendl. & Drude"; Journal of Horticultural Science and Biotechnology (2008) 83(1):33-36.

Nagano, et al.; "Seed germinability in Musa velutina Wendl. & Drude is markedly lowered by 1 week in dry-storage"; Journal of Horticultural Science and Biotechnology (2009) 84(3):325-328.

Nath, Ujjal Kumar et al., Early, non-destructive selection of microspore-derived embryo genotypes in oilseed rape (*Brassica napus* L.) by molecular markers and oil quality analysis, Mol. Breeding (2007) vol. 19(3):285-289.

Nery, et al.; "Cryopreservation of Anadenanthera colubrina (Vell.) brenan embryonic axes"; Acta Horticulturae (2011) 908:227-232.

Neya, et al.; "Ageing increases the sensitivity of neem (*Azadirachta indica*) seeds to imbibitional stress"; Seed Science Research (2004) 14(2)205-217.

Nogueira, et al.; "Cryopreservation of Byrsonima intermedia A. Juss. embryos using different moisture contents"; Acta Horticulturae (2011) 908:199-202 (2011).

Ntuli, et al.; "Increased Drying Rate Lowers the Critical Water Content for Survival in Embryonic Axes of English Oak (*Quercus robur* L.) Seeds"; Journal of Integrative Plant Biology (2011) 53(4):270-280; Institute of Botany, Chinese Academy of Sciences (2011).

Obroucheva, et al.; "Vacuolar status and water relations in embryonic axes of recalcitrant aesculus hippocastanum seeds during stratification and early germination"; AoB Plants (2012)12(1), art. No. pls008.

Ochatt; "Immature seeds and embryos of Medicago truncatula cultured in vitro"; Methods in molecular biology (Clifton, N.J.) (2011) 710:39-52.

Palumbi, et al.; "The Simple Fool's Guide to PCR", University of Hawaii, (2002) version 2.0, pp. 1-45.

Pammenter and Berjak; "Physiology of desiccation-sensitive (recalcitrant) seeds and the implications for cryopreservation"; International Journal of Plant Sciences; (2014) 175(1): 21-28; The University of Chicago, Chicago, IL US.

Percy, et al.; "Desiccation, cryopreservation and water relations parameters of white spruce (*Picea glauca*) and interior spruce (*Picea glauca* x engelmannii complex) somatic embryos"; Tree Physiology (2001) 21(18):1303-1310; Oxford University Press, Oxford, UK.

Plachno and Swiatek; "Unusual embryo structure in viviparous Utricularia nelumbifolia, with remarks on embryo evolution in genus Utricularia"; Protoplasma (2010) 239(1-4):69-80; Springer-Verlag; Berlin/Heidelberg, Germany.

Pond, et al.; "Improving tolerance of somatic embryos of Picea glauca to flash desiccation with a cold treatment (desiccation after cold acclimation)"; In Vitro Cellular and Developmental Biology—Plant (2002) 38(4):334-341; Springer; Germany.

Radha, et al.; "Cryopreservation of excised embryonic axes of Nothapodytes nimmoniana (Graham) Mebberly—A vulnerable medicinal tree species of the Western Ghats"; Indian Journal of Biotechnology (2010) 9(4):435-437.

Rai, et al.; "Effect of ABA and sucrose on germination of encapsulated somatic embryos of guava (*Psidium guajava*L.)"; Scientia Horticulturae (2008) 117(3):302-305; Elsevier B.V.; Amsterdam, The Netherlands.

Rai, et al.; "The role of abscisic acid in plant tissue culture: A review of recent progress"; Plant Cell, Tissue and Organ Culture (2011) 106(2):179-190; Springer Science+Business Media B.V.; Berlin/Heidelberg, Germany (2011).

Rajaee, et al.; "Cryopreservation of embryonic axes of Ferula gummosa: A tool for germplasm conservation and germination improvement"; Acta Horticulturae (2012) 964:153-160.

Rakotondranony, et al.; "Seed storage responses in four species of the threatened genus *Ravenea (Arecaceae)*"; Seed Science and Technology (2006) 34(2):513-517.

Reed and Hummer; "Long-term storage of hazelnut embryonic axes in liquid nitrogen"; Acta Horticulturae (2001) 556:177-180.

Reid and Walker-Simmons; "Group 3 late embryogenesis abundant proteins in desiccation-tolerant seedlings of wheat (*Triticum aestivum* L.)"; Plant Physiology (1993) 102(1):125-131; American Society of Plant Biologists (ASPB); Rockville, MD US.

Rider, et al.; "Metabolic profiling of the *Arabidopsis* pkl mutant reveals selective derepression of embryonic traits"; Planta (2004) 219(3):489-499; Springer-Verlag; Berlin/Heidelberg, Germany.

(56) References Cited

OTHER PUBLICATIONS

Roschzttardtz, et al.; "Identification of the endodermal vacuole as the iron storage compartment in the *Arabidopsis* embryo"; Plant Physiology (2009) 151(3):1329-1338; American Society of Plant Biologists; Rockville, MD US.

Sanchez, et al.; "Preservation of Quercus robur germplasm by cryostorage of embryogenic cultures derived from mature trees and RAPD analysis of genetic stability"; Cryo-Letters (2008) 29(6):493-504; CryoLetters, c/o University of Bedfordshire.

Sangtong, et al.; "Serial Extraction of Endosperm Drillings (SEED)—A Method for Detecting Transgenes and Proteins in Single Viable Maize Kernels"; Plant Molecular Biology Reporter (2001) 19(2):151-158.

Santos and Stushnoff; "Desiccation and freezing tolerance of embryonic axes from Citrus sinensis [L.] osb. pretreated with sucrose"; Cryo-Letters (2003) 24(5):281-292.

Schaeffer, et al.; "Segregation for endosperm lysine in F2, F3 and F4 progeny from a cross of in vitro-selected and unselected cultivar of rice"; Theoretical and Applied Genetics (1989) 77(2):176-183; Springer-Verlag; Berlin/Heidelberg, Germany.

Schwienbacher, et al.; "Seed dormancy in alpine species"; Flora: Morphology, Distribution, Functional Ecology of Plants (2011) 206(10):845-856; Elsevier GmbH; Amsterdam, The Netherlands.

Seran, et al.; "Encapsulation of embryonic axes of Camellia sinensis (L.) O. *Kuntze* (tea) and subsequent in vitro germination"; Journal of Horticultural Science and Biotechnology (2005) 80(1):154-158.

Sharma, et al.; "ABA associated biochemical changes during somatic embryo development in Camellia sinensis (L) O. Kuntze"; Journal of Plant Physiology (2004) 161(11):1269-1276; Elsevier GmbH; Amsterdam, The Netherlands.

Sopory, et al.; "Early protein synthesis during germination of barley embryos and its relationship to RNA synthesis"; Plant and Cell Physiology (1980) 21(4):649-657; Oxford University Press; Oxford, UK.

Sreedhar, et al.; "In vivo characterization of the effects of abscisic acid and drying protocols associated with the acquisition of desiccation tolerance in alfalfa (*medicago sativa* L) Somatic embryos"; Annals of Botany (2002) 89(4):391-400; Annals of Botany Company; Oxford, UK.

Steinmacher, et al.; "Cryopreservation of peach palm zygotic embryos"; Cryo-Letters (2007) 28(1):13-22; CryoLetters, c/o Royal Veterinary College.

Sulusoglu; Development of embryo culture protocol for cherry laurel (*Prunus laurocerasus* L.); Journal of Food, Agriculture and Environment (2012) 10(3-4): 347-352.

Tahir, et al.; "Identification and characterization of PgHZ1, a novel homeodomain leucine-zipper gene isolated from white spruce (*Picea glauca*) tissue"; Plant Physiology and Biochemistry (2008) 46(12):1031-1039; Elsevier Masson SAS; Oxford, UK.

Vieitez, et al.; "Cryopreservation of zygotic embryonic axes and somatic embryos of European chestnut"; Methods in molecular biology (Clifton, N.J.) (2011) 710:201-213.

Wagner; "Changes in dormancy levels of Fraxinus excelsior L. embryos at different stages of morphological and physiological maturity"; Trees—Structure and Function (1996) 10(3):177-182.

Wan, Y. et al.; "Efficient production of doubled haploid plants through colchicine treatment of anther-derived maize callus", Theor. Appl. Genet. (1989) 77:889-892.

Wan, Y. et al., "The use of antimicrotubule herbicides for the production of doubled haploid plants from anther-derived maize callus", Theor. Appl. Genet (1991) 81:205-211.

Wen, et al.; "Differential responses of Mimusops elengi and Manilkara zapota seeds and embryos to cryopreservation"; In Vitro Cellular and Developmental Biology—Plant (2013) 49(6):717-723; Springer, Germany.

Wesley-Smith, et al.; "Interactions among water content, rapid (nonequilibrium) cooling to—196° C., and survival of embryonic axes of Aesculus hippocastanum L. seeds"; Cryobiology (2001) 42(3):196-206; Academic Press.

Xia and Kermode; "Analyses to determine the role of embryo immaturity in dormancy maintenance of yellow cedar (*Chamaecyparis nootkatensis*) seeds: Synthesis and accumulation of storage proteins and proteins implicated in desiccation tolerance"; Journal of Experimental Botany (1999) 50(330):107-118; Society for Experiemental Biology; Southhampton, UK.

Xu, et al.; "Abscisic acid and osmoticum prevent germination of developing alfalfa embryos, but only osmoticum maintains the synthesis of developmental proteins"; Planta (1990) 182(3):382-390; Springer-Verlag; Berlin/Heidelberg, Germany.

Yamakawa, et al., "Production of Anthocyanins by Vitis Cells in Suspension Culture", Agric. Biol. Chem. (1983) 47(10):2185-2191.

Zarek; "A practical method for overcoming the dormancy of Taxus baccata isolated embryos under in vitro conditions"; In Vitro Cellular and Developmental Biology—Plant (2007) 43(6):623-630; Springer, Germany.

Zeng, et al.; "Cryopreservation study on seeds and embryos in Dalbergia odorifera"; Zhongguo Zhongyao Zazhi (2014) 39(12):2263-2266.

Zhang, et al.; "Optimizing seed water content: Relevance to storage stability and molecular mobility"; Journal of Integrative Plant Biology (2010) 52(3):324-331; 2010 Institute of Botany, Chinese Academy of Sciences.

Zi, et al.; "Proteomics study of rice embryogenesis: Discovery of the embryogenesis-dependent globulins"; Electrophoresis (2012) 33(7):1129-1138; WILEY-VCH Verlag GmbH & Co. KGaA, Weinheim.

The International Search Report and Written Opinion of the International Searching Authority for PCT/US2015/034145, dated Aug. 27, 2015.

Cruz-Cruz, Carlos Alberto et al., "Biotechnology and Conservation of Plant Biodiversity", Resources, 2013, vol. 2(2): 73-95.

Withers, Lyndsey A., "In-vitro conservation", Biological Journal of the Linnean Society, 1991, vol. 43 (1): 31-42.

Sharma, Neelam et al., "In vitro conservation of Bacopa monnieri (L.) using mineral oil", Plant Cell, Tissue and Organ Culture, 2012, vol. 111(3):291-301.

The International Search Report and Written Opinion of the International Searching Authority for PCT/US2015/034129, dated Aug. 5, 2015.

Abdalla and Roberts; "Effects of temperature, moisture, and oxygen on the induction of chromosome damage in seeds of barley, broad beans, and peas during storage"; Annals of Botany (1968) 32(1):119-136; Oxford University Press; Oxford UK.

Adachi, et al.;"Crystal structure of soybean 11S globulin: Glycinin A3B4 homohexamer"; Proceedings of the National Academy of Sciences of the United States of America (2003) 100(12):7395-7400.

Banilas, et al.; "Oleosin di-or tri-meric fusions with GFP undergo correct targeting and provide advantages for recombinant protein production"; Plant Physiology and Biochemistry (2011) 49(2):216-222; Elsevier Masson SAS; Oxford, UK.

Beardmore and Vong, "Role of the cotyledonary tissue in improving low and ultralow temperature to tolerance of butternut (*Juglans cinerea*) embryonic axes"; Canadian Journal of Forest Research (1998) 28(6):903-910.

Bozorgipour and Snape; "The assessment of in vitro characters and their influence on the success rates of doubled haploid production in barley"; Euphytica (1991) 58(2):137-144; Springer; The Netherlands.

Brownfield, et al.; "Patterns of storage protein and triacylglycerol accumulation during loblolly pine somatic embryo maturation"; Plant Cell, Tissue and Organ Culture (2007) 88(2):217-223; Springer Science+Business Media B.V.; Berlin/Heidelberg, Germany.

Busk and Pages; "Microextraction of Nuclear Proteins from Single Maize Embryos"; Plant Molecular Biology Reporter (1997) 15:371-376; Kluwer Academic Publishers; Belguim.

Capuna, et al.; "Plant regeneration of common ash (*Fraxinus excelsior* L.) by somatic embryogenesis"; In Vitro Cellular and Developmental Biology—Plant (2007) 43(2):101-110; The Society for In Vitro Biology.

(56) References Cited

OTHER PUBLICATIONS

Carasso, et al.; "A threatened alpine species, Fritillaria tubiformis subsp. moggridgei: Seed morphology and temperature regulation of embryo growth"; Plant Biosystems (2012) 146(1):74-83; Taylor and Francis Group, LLC.

Chia, et al.; "Storage oil breakdown during embryo development of *Brassica napus* (L.)"; Journal of Experimental Botany, (2005) 56(415):1285-1296; Oxford University Press; Southhampton, UK.

Cho, et al.; "Cryopreservation of Citrus aurantifolia seeds and embryonic axes using a desiccation protocol"; Cryo-Letters (2002) 23(5):309-316.

Corredoira, et al.; "Cryopreservation of zygotic embryo axes and somatic embryos of European chestnut"; Cryo-Letters (2004) 25(1):33-42.

Corredoira, et al.; "Genetic transformation of European chestnut somatic embryos with a native thaumatin-like protein (CsTL1) gene isolated from Castanea sativa seeds"; Tree Physiology (2012) 32(11):1389-1402; Oxford University Press; Oxford UK.

Crouch and Sussex; "Development and storage-protein synthesis in *Brassica napus* L. embryos in vivo and in vitro"; Planta (1981) 153(1):64-74; Springer-Verlag; Berlin/Heidelberg, Germany.

Da Rosa, et al.; "Inhibition of in vitro development of Coffea embryos by exogen caffeine [Inibição do desenvolvimento in vitro de embriões de Coffea por cafeína exógena]"; Revista Brasileira de Sementes (2006) 28(3):177-184.

Di Nola and Mayer, et al.; "Effect of temperature on glycerol metabolism in membranes and on phospholipases C and D of germinating pea embryos"; Phytochemistry (1986) 25(10):2255-2259.

Dolce, et al.; "Enhanced seed germination of Ilex dumosa R. (*Aquifoliaceae*) through in vitro culture of cut pyrenes"; HortScience (2011) 46(2):278-281.

El-Sharkawi, et al.; "Trifactorial interactive effects of nutrients, water potential and temperature on carbohydrate allocation to the embryonic axis of desert plant seeds"; Journal of Arid Environments (1997) 35(4):655-664.

Fang, et al.; "Influence of freezable/non-freezable water and sucrose on the viability of Theobroma cacao somatic embryos following desiccation and freezing"; Plant Cell Rep (2009) 28:883-889; Springer; Berlin/Heidelberg, Germany.

Faria, et al.; "Physiological and cytological aspects of Inga vera subsp. affinis embryos during storage"; Brazilian Journal of Plant Physiology (2006) 18(4):503-513.

Farnsworth; "The ecology and physiology of viviparous and recalcitrant seeds"; Annual Review of Ecology and Systematics (2000) 31:107-138.

Fernando, et al.; "Identifying dormancy class and storage behaviour of champak (*Magnolia champaca*) seeds, an important tropical timber tree"; Journal of the National Science Foundation of Sri Lanka; (2013) 41(2):141-146.

Gifford, et al.; "Control by the embryo axis of the breakdown of storage proteins in the endosperm of germinated castor beanseed: A role for gibberellic acid"; Journal of Experimental Botany, (1984) 35(5):669-677; Oxford University Press; Oxford UK.

Gonzalez-Benito, "Cryopreservation as a tool for preserving genetic variability: Its use with Spanish wild species with possible landscaping value"; Acta Horticulturae (1998) 457:133-142.

Gonzalez-Benito, et al.; "The development of a protocol for the encapsulation-desiccation and in vitro culture of embryonic axes of Quercus suber L. and Q. ilex L."; Silvae Genetica (1999) 48(1):25-28.

Gumilevskaya and Azarkovich; "Physiological and biochemical characteristics of the recalcitrant seeds having dormancy: A review"; Applied Biochemistry and Microbiology (2007) 43(3):332-340; Nauka/Interperiodica.

Hajari, et al.; "A novel means for cryopreservation of germplasm of the recalcitrant-seeded species, Ekebergia capensis"; Cryo-Letters (2011) 32(4):308-316.

Holtman, et al.; "Lipoxygenase-2 oxygenates storage lipids in embryos of germinating barley"; European Journal of Biochemistry (1997) 248(2):452-458.

Hu, et al.; "Seed dormancy in four Tibetan Plateau Vicia species and characterization of physiological changes in response of seeds to environmental factors"; Seed Science Research, (2013) 23(2):133-140; Cambridge University Press; Cambridge UK.

Ipekci and Gozukirmizi; "Direct somatic embryogenesis and synthetic seed production from Paulownia elongata"; Plant Cell Reports (2003) 22(1):16-24; Springer; Berlin/Heidelberg, Germany.

Ishikawa, et al.; "Cryopreservation of zygotic embryos of a Japanese terrestrial orchid (*Bletilla striata*) by vitrification"; Plant Cell Reports (1997) 16(11):754-757; Springer; Berlin/Heidelberg, Germany.

Jayasanker, et al.; "Low temperature storage of suspension culture-derived grapevine somatic embryos and regeneration of plants"; In Vitro Cellular and Developmental Biology—Plant (2005) 41(6):752-756; Springer, Germany.

Kainer, et al.; "Moist storage of Brazil nut seeds for improved germination and nursery management"; Forest Ecology and Management (1999) 116(1-3):207-217.

Kersulec, et al.; "Physiological behaviour of encapsulated somatic embryos"; Biomaterials, Artificial Cells, and Immobilization Biotechnology (1993) 21(3):375-381.

Kim, et al.; "Cryopreservation of tea (*Camellia sinensis* L.) seeds and embryonic axes"; Cryo-Letters (2002) 23(4):209-216.

Kovalchuk, et al.; "Cryopreservation of native kazakhstan apricot (Pr Unus Armenia Ca L) seeds and embryonic axes"; Cryo-Letters (2014) 35(2):83-89.

Krishna, Kumar and Thomas, "High frequency somatic embryogenesis and synthetic seed production in Clitoria ternatea Linn"; Plant Cell, Tissue and Organ Culture, (2012) 110(1):141-151; Springer Science+ Business Media B.V.; Berlin/Heidelberg, Germany.

Kriz; "Characterization of embryo globulins encoded by the maize Glb genes"; Biochemical Genetics (1989) 27 (3-4):239-251; Plenum Publishing Corporation.

Lai and Mckersie; "Effect of nutrition of maturation of alfalfa (*Medicago sativa* L.) somatic embryos"; Plant Science (1993) 91(1):87-95; Elsevier; Oxford, UK.

Lai and Mckersie; "Regulation of starch and protein accumulation in alfalfa (*Medicago sativa* L.) somatic embryos"; Plant Science (1994) 100(2):211-219; Elsevier; Oxford, UK.

Lelu-Walter, et al.; "Simplified and improved somatic embryogenesis for clonal propagation of Pinus pinaster (Ait.)"; Plant Cell Reports (2006) 25(8):767-776; Springer-Verlag; Berlin/Heidelberg, Germany.

Li and Foley; "Cloning and characterization of differentially expressed genes in imbibed dormant and afterripened Avena fatua embryos"; Plant Molecular Biology (1995) 29(4):823-831; Springer, The Netherlands.

Long, et al.; "Maturation and germination of Phaseolus vulgaris embryonic axes in culture"; Planta (1981) 153(5):405-415; Springer-Verlag; Berlin/Heidelberg, Germany.

Lopez-Molina, et al.; "A postgermination developmental arrest checkpoint is mediated by abscisic acid and requires the ABI5 transcription factor in *Arabidopsis*"; Proceedings of the National Academy of Sciences of the United States of America (2001) 98(8):4782-4787.

Malik, et al.; "Long-term, large scale banking of citrus species embryos: Comparisons between cryopreservation and other seed banking temperatures"; Cryo-Letters (2012) 33(6):453-464.

Maqsood, et al.; "Synthetic seed development and conversion to plantlet in catharanthus roseus (L.) G. Don."; Biotechnology (2012) 11(1):37-43; Asian Network for Scientific Information.

Martin and Northcote; "Qualitative and quantitative changes in mRNA of castor beans during the initial stages of germination"; Planta (1981) 151(2):189-197; Springer-Verlag; Berlin/Heidelberg, Germany.

Mathieu, et al.; "Cloning of a pine germin-like protein (GLP) gene promoter and analysis of its activity in transgenic tobacco Bright Yellow 2 cells"; Physiologia Plantarum (2003) 117(3):425-434; Munksgaard International Publishers Ltd; Copenhagen, Denmark.

(56) References Cited

OTHER PUBLICATIONS

Mieryk; "Seed Proteomics"; Methods in Molecular Biology (2014) 1072:361-377; Springer; Berlin/Heidelberg, Germany.
Mroginski, et al.; "A cryopreservation protocol for immature zygotic embryos of species of Ilex (Aquifoliaceae)"; Biocell (2008) 32(1):33-39.

* cited by examiner

Figure 1: Endpoint Fluorescence Scatter Plot

Figure 3: Endpoint Fluorescence Scatter Plot

Figure 4: Endpoint Fluorescence Scatter Plot

Figure 8: Endpoint Fluorescence Scatter Plot

Figure 10: Endpoint Fluorescence Scatter Plot

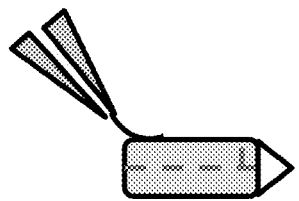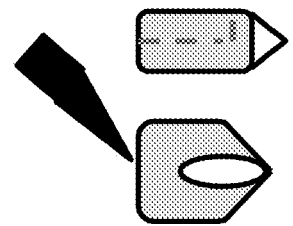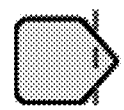
FIGURE 14

Figure 16: Endpoint Fluorescence Scatter Plot

PLANT EMBRYO STORAGE AND MANIPULATION

CROSS REFERENCE TO RELATED APPLICATIONS

This application claims the benefit of U.S. Pat. No. 9,078,427, which is incorporated by reference in its entirety.

BACKGROUND OF THE INVENTION

It is conventional practice in plant breeding to grow plants from seed of known parentage. Seed are planted in experimental plots, growth chambers, greenhouses, or other growing conditions and plants arising from the seed are either cross pollinated with other plants of known parentage or self-pollinated. The resulting seed are the offspring of the two parent plants or the self-pollinated plant, and are harvested, processed and planted to continue the plant breeding cycle. Specific laboratory or field-based tests may be performed on the plants, plant tissues, seed or seed tissues, in order to aid in the breeding process.

Generations of plants based on known crosses or self-pollinations are planted and then tested to see if these lines or varieties are moving towards characteristics that are desirable in the marketplace. Examples of desirable traits include, but are not limited to, increased yield, increased homozygosity, improved or newly conferred resistance and/or tolerance to specific herbicides and/or pests and pathogens, increased oil content, altered starch content, nutraceutical composition, drought tolerance, and specific morphological based trait enhancements.

As can be appreciated and as is well known in the art, these experiments can be massive in scale. They involve a huge labor force ranging from scientists to field staff to design, plant, maintain, and conduct the experiments, which can involve thousands or tens of thousands of individual plants. They also require substantial land resources. Plots or greenhouses can take up thousands of acres of land. Not only does this tie up large amounts of land for months while the plants germinate, grow, and produce seed, during which time they may be tested in the laboratory or field, but then the massive amounts of seed must be individually tagged, harvested and processed.

A further complication is that much of the experimentation goes for naught. It has been reported in the literature that some seed companies discard 80-90% of the plants early on in the experiment. Thus, much of the land, labor and material resources expended for growing, harvesting, and post-harvest processing ultimately are wasted for a large percentage of the seed.

Timing pressures are also a factor. Significant advances in plant breeding have put pressure on seed companies to quickly advance lines or varieties of plants that have more and better traits and characteristics. The plant breeders and associated workers are thus under increasing pressure to more efficiently and effectively process these generations and make significant selections early on in the breeding process.

Therefore, a movement towards earlier identification of traits of interest through laboratory based seed testing has emerged. Seed is non-destructively tested to derive genetic, biochemical or phenotypic information. If traits of interest are identified, the selected seed from specific plants are used either for further experiments and advancement, or to produce commercial quantities. Testing seed prevents the need to grow the seed into immature plants, which are then tested. This saves time, space, and effort. If effective, early identification of desirable traits in seed can lead to a great reduction in the amount of land needed for experimental testing, the amount of seed that must be tested, and the amount of time needed to derive the information necessary for making advancement decisions. For example, instead of thousands of acres of plantings and the subsequent handling and processing of all those plants, a fraction of acres and plants might be enough. However, because timing is still important, this is still a substantial task because even such a reduction involves processing, for example, thousands of seed per day.

A conventional method of attempting non-lethal seed testing is as follows: a single seed of interest is held with pliers above a sheet of paper laid out on a surface; a small drill bit is used to drill into a small location on the seed; debris is removed by the drill bit and collected on a sheet of paper; the paper is lifted; and the debris is transferred to a test tube or other container for subsequent laboratory analysis. This method is intended to be non-lethal to the seed. However, the process is slow, and its success and effectiveness depends heavily on the attention and accuracy of the worker. Each single seed must be manually picked up and held by the pliers. The drilling is also manual. Care must be taken with the drilling and the handling of the debris. Single containers, e.g. the individual test tubes, must then be handled and marked or otherwise tracked and identified. Additionally, the pliers and drill must be cleaned between the testing of each seed. There can be substantial risk of contamination by carry-over from seed to seed and the manual handling. Also, many times it is desirable to obtain seed material from a certain physiological tissue of the seed. For example, with corn seed, it may be desirable to genotype the endosperm. In such cases, it is not trivial, but rather is time-consuming and somewhat difficult, to manually grasp a small corn seed in such a way to allow the endosperm to be oriented to expose it for drilling. Testing other seed structures such as the seed germ is preferably avoided because removing material from such regions of the seed negatively impacts germination rates. Sometimes it is difficult to obtain a useful amount of material with this method.

Another example of non-lethally obtaining tissue from corn seed for laboratory analysis is disclosed at V. Sangtong, E. C. Mottel, M. J. Long, M. Lee, and M. P. Scott, Serial Extraction of Endosperm Drillings (SEED)—A Method for Detecting Transgenes and Proteins in Single Viable Maize Kernels, *Plant Molecular Biology Reporter* 19: 151-158, June 2001, which is incorporated by reference herein. It describes use of a hand-held rotary grinder to grind off particles, called "drillings," from the kernel and collection of the particles to test for the presence of certain genes. However, this method also requires manual grasping and orientation of each individual seed relative to the grinder. It, too is time consuming and somewhat cumbersome. It also relies on the skill of the worker. This method raises issues of throughput, accuracy, whether a useful amount of material is obtained, and contamination. The grinder must be thoroughly cleaned between kernels in order to prevent contamination.

As evidenced by these examples, present conventional seed analysis methods used in genetic, biochemical, or phenotypic analysis, require at least a part of the seed to be removed and processed. In removing some seed tissue, various objectives may need to be met. These may include one or more of the following objectives:

(a) maintain seed viability after collection of seed tissue, if required.

(b) obtain at least a minimum required amount of tissue, without affecting viability.

(c) obtain tissue from a specific location on the seed, often requiring the ability to orient the seed in a specific position.

(d) maintain a particular throughput level for efficiency purposes.

(e) reduce or virtually eliminate contamination.

(f) allow for the tracking of separate tissues and their correlation to seeds from which the tissues were obtained.

(a) Viability

With regard to maintaining seed viability, it may be critical in some circumstances that the seed tissue removal method and apparatus not damage the seed in such a way that seed viability is reduced. It is often desirable that such analysis be non-lethal to the seed, or at least result in a substantial probability that the seed will germinate (e.g. no significant decrease in germination potential) so that it can be grown into a mature plant. For some analyses, seed viability does not need to be maintained, in which case larger quantities of tissue can often be taken. The need for seed viability will depend on the intended use of the seeds.

(b) Tissue Quantity

It is desirable to obtain a useful amount of tissue. To be useful, it must be above a certain minimum amount necessary in order to perform a given test and obtain a meaningful result. Different tests or assays require different quantities of tissue. It may be equally important to avoid taking too much tissue to avoid reducing germination potential of a seed, which may be undesirable. Therefore, it is desirable that the apparatus and methods for removing the seed tissue allow for variation in the amount of tissue taken from any given seed.

(c) Tissue Location

A useful amount of tissue also can involve tissue location accuracy. For example, in some applications the tissue must come only from a certain seed location or from specific tissue. Further, it is difficult to handle small particles like many seeds. It is also difficult to accurately position and orient seed. On a corn seed, for example, it may be important to test the endosperm tissue, and orient the corn seed for optimal removal of the endosperm tissue. Therefore, it is desirable that the apparatus and methods for removing the seed tissue are adapted to allow for location-specific removal, which may include specific seed orientation methods.

(d) Throughput

An apparatus and methodology for seed tissue removal must consider the throughput level that supports the required number of tissues to be taken in a time efficient manner. For example, some situations involve the potential need to test thousands, hundreds of thousands, or even millions of seed per year. Taking the hypothetical example of a million seed per year, and a 5-day work week, this would average nearly four thousand tests per day for each working day of a year. It is difficult to meet such demand with lower throughput methods. Accordingly, higher throughput, automatic or even semi-automatic methods for removal of seed tissue may be desirable.

(e) Avoiding Contamination

It is desirable that an apparatus and methodology for seed tissue removal not be prone to cross-contamination in order to maintain purity for subsequent analytical testing procedures. This can involve not only tissue location accuracy, such that tissue from a given location is not contaminated with tissue from a different location, but also methods involved in the removal and handling of the tissue to be tested, ensuring no contamination.

(f) Tracking Tissue to be Tested

Efficient processing of seeds and tissue removed from seeds presents a variety of challenges, especially when it is important to keep track of each seed, the tissue removed from such, and their correlation to each other, or to other tissues. Accordingly, it is desirable that apparatus and methods for tissue removal and testing allow for easy tracking of seed and tissue removed from such.

Conventional seed testing technologies do not address these requirements sufficiently, resulting in pressures on capital and labor resources, and thus illustrate the need for an improvement in the state of the art. The current methods are relatively low throughput, have substantial risk of cross-contamination, and tend to be inconsistent because of a reliance on significant manual handling, orienting, and removal of the tissue from the seed. This can affect the type of tissue taken from the seed and the likelihood that the seed will germinate. There is a need to eliminate the resources current methods require for cleaning between removal of individual portions of seed tissue. There is a need to reduce or minimize cross-contamination between unique tissue portions to be tested by carry-over or other reasons, or any contamination from any source of any other tissue. There is also a need for more reliability and accuracy. Accordingly, there is a need for methodologies and their corresponding apparatus which provide for seed tissue removal and testing that accomplishes one or more of the following objectives:

(a) maintains seed viability after seed tissue removal.

(b) obtains at least a minimum required amount of tissue, without affecting viability.

(c) obtains tissue from a specific location on the seed.

(d) maintains a particular throughput level for efficiency purposes.

(e) reduces or virtually eliminate contamination.

(f) allows for the tracking of separate tissues and their correlation to seeds from which the tissues were obtained.

Some of these objectives can be conflicting and even antagonistic. For example, obtaining a useful amount of tissue while maintaining seed viability requires taking some seed tissue, but not too much. Moreover, high-throughput methodologies involve rapid operations but may be accompanied by decreases in accuracy and increased risk of contamination, such that the methods must be done more slowly than is technically possible in order to overcome the limitations. These multiple objectives have therefore existed in the art and have not been satisfactorily addressed or balanced by the currently available methods and apparatuses. There is a need in the art to overcome the above-described types of problems such that the maximum number of objectives is realized in any given embodiment.

SUMMARY

The invention includes methods for analyzing plant material, and specifically seed tissue, while preserving viability of the seed or embryo (i.e. can form a plant). The method may include the steps of collecting shed cellular material from one or more embryos; obtaining genetic material such as DNA from the shed cellular material; performing a molecular analysis of the genetic material; and germinating at least one of said one or more embryos. The one or more embryos may be immature. In one embodiment, the shed cellular material is collected from an embryo by agitating the embryo in a non-destructive medium such as water or other aqueous solution. In some embodiments, DNA may be obtained from the shed cellular material by exposing the shed cellular material to cold and then heat followed by agitation; the steps may be repeated. In other embodiments, DNA may be obtained from the shed cellular material by heating of the shed cellular material and agitation; the steps may be repeated. In other embodiments, DNA may be obtained by incubating the shed cellular material with an enzyme; the enzyme may be VISCOZYME® L, a multi-enzyme complex containing a wide range of carbohydrases, including arabanase, cellulase, β-glucanase, hemicellulase, and xylanase. (See the Sigma Aldrich product catalog). In still other embodiments, DNA may be obtained using DNA extraction techniques, such as but not limited to the use of magnetic particles that bind genetic material or any method known to one of ordinary skill in the art.

The methods of the invention include obtaining genetic material from embryos and performing a molecular analysis of the genetic material while preserving the embryos' ability to germinate. In some embodiments, the embryos are suspended in an aqueous solution surrounded by a matrix of one or more oils. Preferably, at least one of the one or more oils has a density greater than that of the aqueous solution. The one or more embryos may be immature. In some embodiments, antimicrobial agents and/or minimal growth media may be added to the aqueous solution. In some embodiments, the embryos may be stored in cold and/or dark conditions to prevent premature germination. In a preferred embodiment, the embryos are stored at a temperature of approximately 4° C. In some embodiments, the embryos may be transferred for continued storage. In other embodiments, the embryos may be transferred to germination medium, and one or more of the embryos may be germinated. In still other embodiments, an aliquot of the aqueous solution may be removed, genetic material may be obtained from cellular material in the aliquot, and the genetic material may be used for molecular analysis (e.g. to genotype the stored embryos). The molecular analysis may be genotyping, which may occur by way of: single nucleotide polymorphism detection, restriction fragment length polymorphism identification, random amplified polymorphic detection, amplified fragment length polymorphism detection, polymerase chain reaction, DNA sequencing, whole genome sequencing, allele specific oligonucleotide probes, or DNA hybridization to DNA microarrays or beads. Whole genome amplification may be performed prior to the molecular analysis. In other embodiments, one or more of the steps described above may be automated.

Methods of the invention include obtaining embryonic DNA (whether or not said obtaining the embryonic DNA includes extraction), storing the embryo from which the DNA was extracted in a manner that preserves the embryo's ability to germinate and grow into a plant, genotyping the embryo using the embryonic DNA, and determining whether to germinate and grow the embryo (i.e. selecting) or to discard the embryo based on its genotype (i.e. counterselecting). An embryo that is selected to germinate and grow based on its genotype may be grown into a plant and phenotyped, used for breeding, or used to bulk up seed of the same genotype. In preferred embodiments, one or more steps of the method may be automated.

One embodiment of the invention allows for determining the maternal lineage of one or more seeds by collecting maternal seed tissue from the one or more seeds; washing the maternal seed tissue; dissociating and homogenizing the maternal seed tissue to obtain a homogenized solution; centrifuging the homogenized solution to obtain supernatant; and performing a molecular analysis using supernatant DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The dissociation and homogenization of pericarp tissue may be performed using a cell dissociator (such as gentleMACS™, Miltenyi Biotec). The method may further comprise using whole genome amplification prior to the molecular analysis to obtain sufficient DNA yield.

Another embodiment of the invention allows for determining the maternal lineage of one or more seeds by collecting maternal seed tissue from the one or more seeds; washing the maternal seed tissue; dissociating and homogenizing the maternal seed tissue to obtain a homogenized solution; extracting DNA from cells contained within the homogenized solution; and performing a molecular analysis of the extracted DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The dissociating and homogenizing step may be performed using a cell dissociator (such as gentleMACS™, Miltenyi Biotec). The extracting step may be performed using DNA-binding magnetic particles or Extract-N-Amp™. The method may further comprise using whole genome amplification prior to the molecular analysis to obtain sufficient DNA yield.

Another embodiment of the invention allows for determining the maternal lineage of one or more seeds by collecting maternal seed tissue from the one or more seeds; washing the maternal seed tissue; disrupting the maternal seed tissue in liquid nitrogen; extracting DNA from the disrupted maternal seed tissue; and performing a molecular analysis of the extracted DNA. In one embodiment, the maternal seed tissue is pericarp. The washing step may be performed with 1 sodium dodecyl sulfate solution, water, ethanol, or mixtures thereof. The washing step is preferably performed with an aqueous solution of about 1% sodium dodecyl sulfate. The extracting step may be performed using DNA-binding magnetic particles or Extract-N-Amp™. The method may further comprise using whole genome amplification prior to the molecular analysis to obtain sufficient DNA yield.

Another embodiment of the invention allows for determining the maternal lineage of one or more seeds by collecting maternal seed tissue from the one or more seeds; washing the maternal seed tissue; extracting DNA directly from the washed maternal seed tissue; and performing a molecular analysis of the extracted DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The extracting step may be performed using Extract-N-Amp™. The method may further comprise using whole genome amplification prior to the molecular analysis to obtain sufficient DNA yield.

In any of the embodiments stated above, the molecular analysis may be genotyping. When maternal seed tissue from more than one seed replicate is collected, a consensus genotype may be obtained.

DESCRIPTIONS OF THE DRAWINGS

In FIGS. 1 through 11, upside down triangles represent samples having one homozygous state; right side up triangles represent samples having the other homozygous state; triangles pointing towards the left represent the heterozygous control; circles represent missing or negative control data; and diamonds represent unquantifiable calls. The tighter the cluster of points is along a line parallel to either axis, the less variation with the method being tested.

Figure 11:
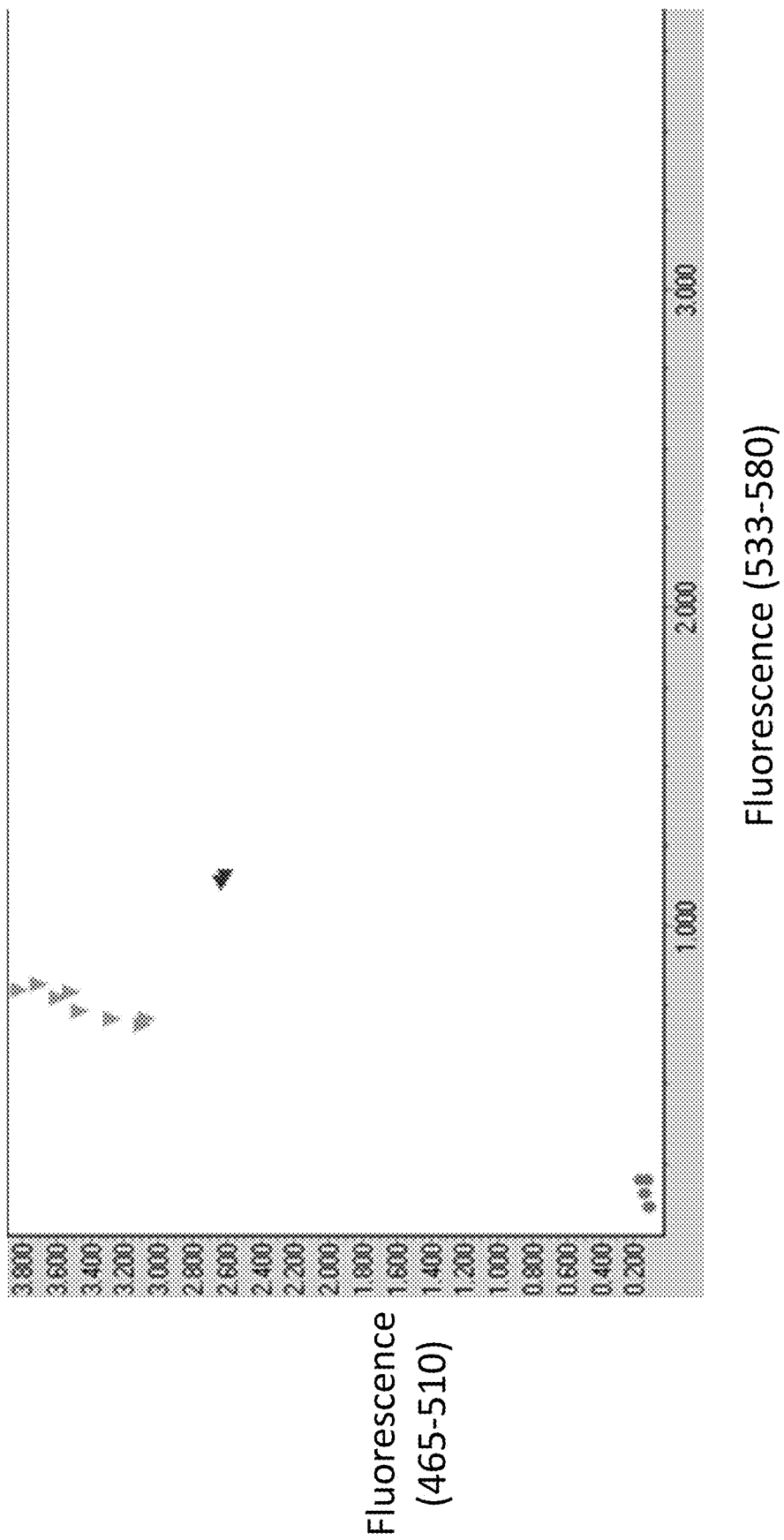

FIG. 11 depicts genotyping data from one marker using DNA obtained with the cold-heat shock treatment and whole genome amplification (using the REPLI-g Single Cell Kit) to obtain sufficient yield of DNA prior to genotyping. The data represents four treatments (incubate only; vortex at speed 3 for 5 seconds; vortex at speed 10 for 5 seconds; and vortex at speed 10 for 30 seconds) in an incubation volume of 10 µL.

Figure 12:
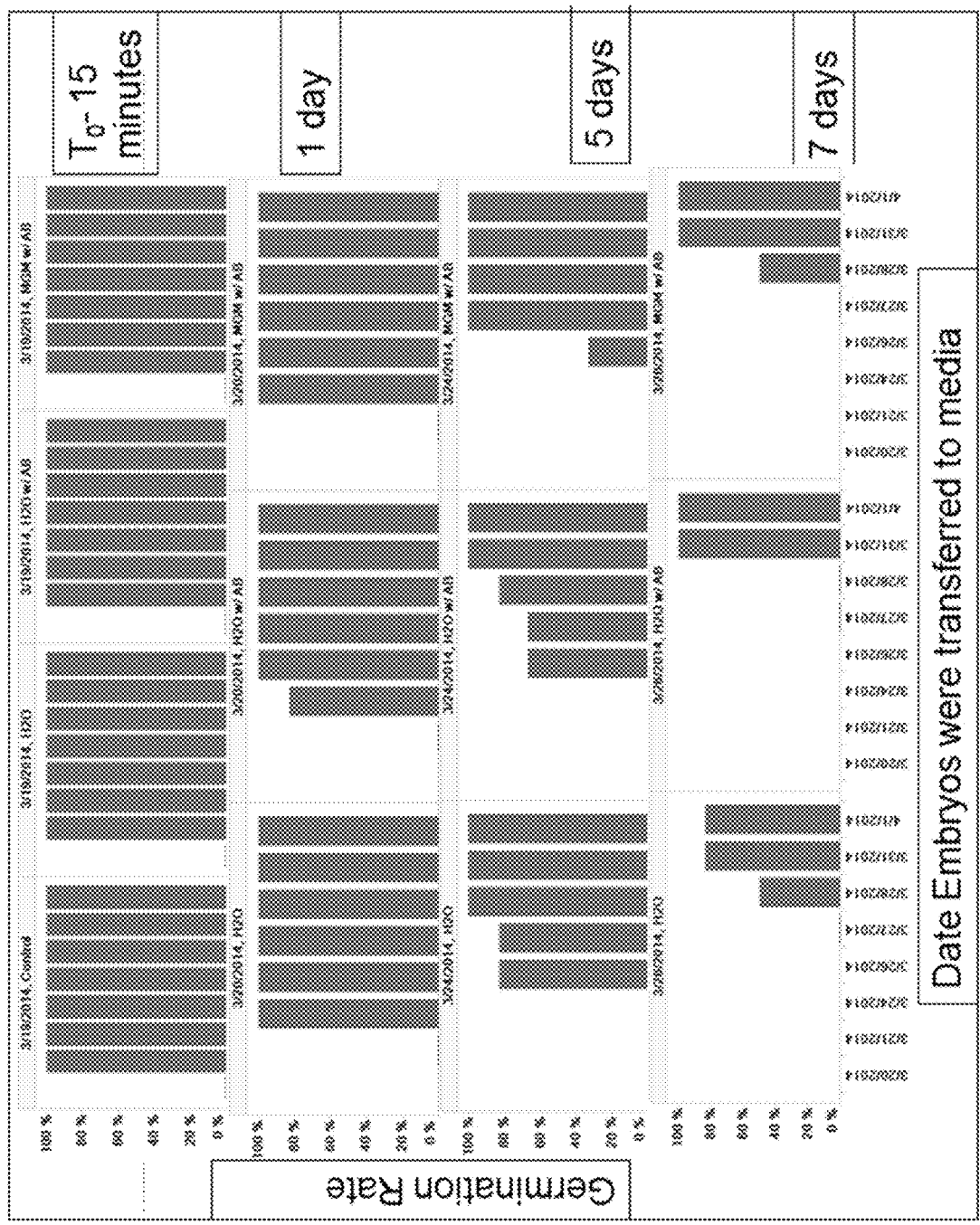

FIG. 12 depicts germination results for embryos of a first maize line, wherein the embryos were stored using methods of the invention.

Figure 13:
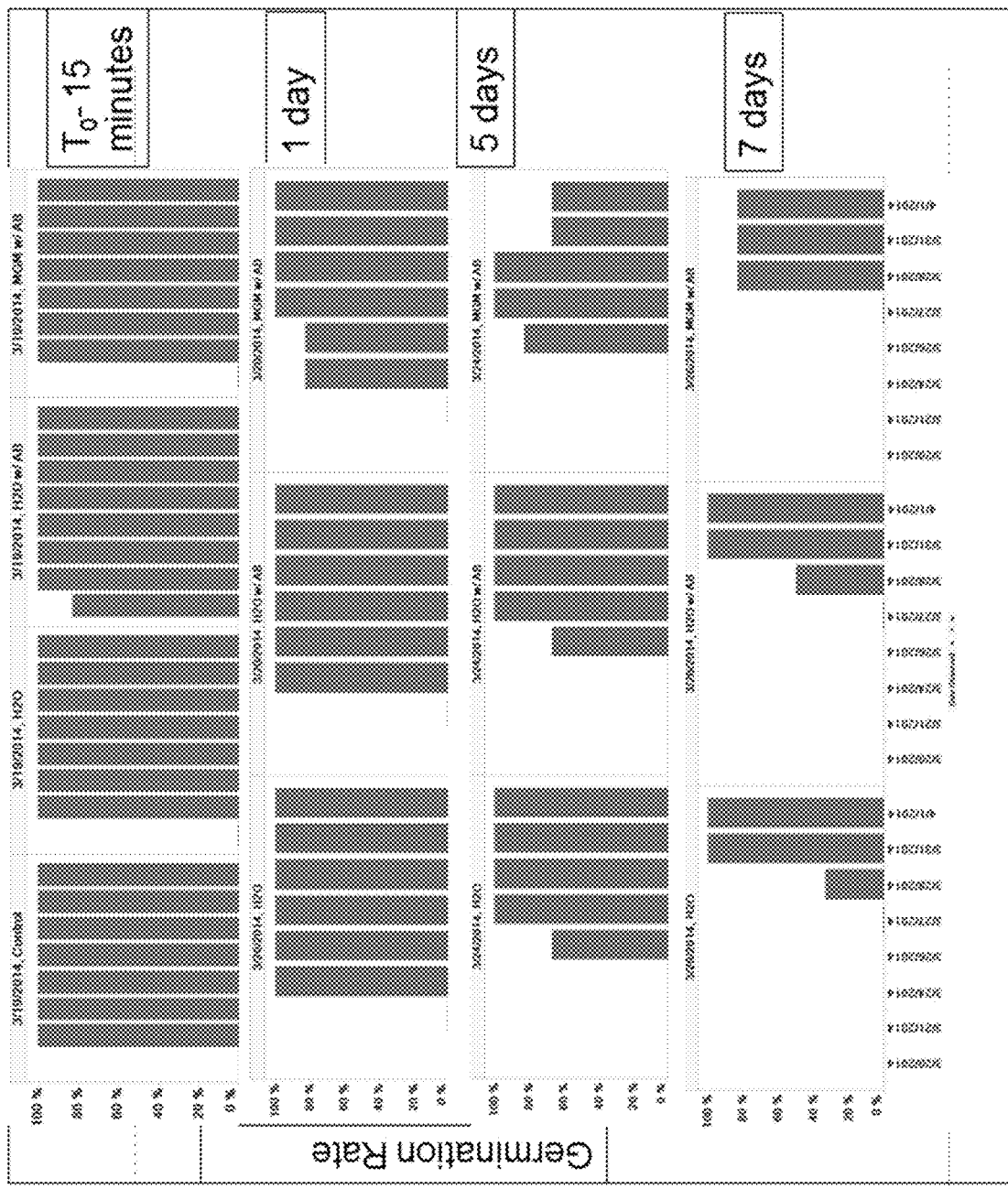

FIG. 13 depicts germination results for embryos of a second maize line, wherein the embryos were stored using methods of the invention.

FIG. 14 depicts the steps involved in peeling of pericarp tissue.

Figure 15:
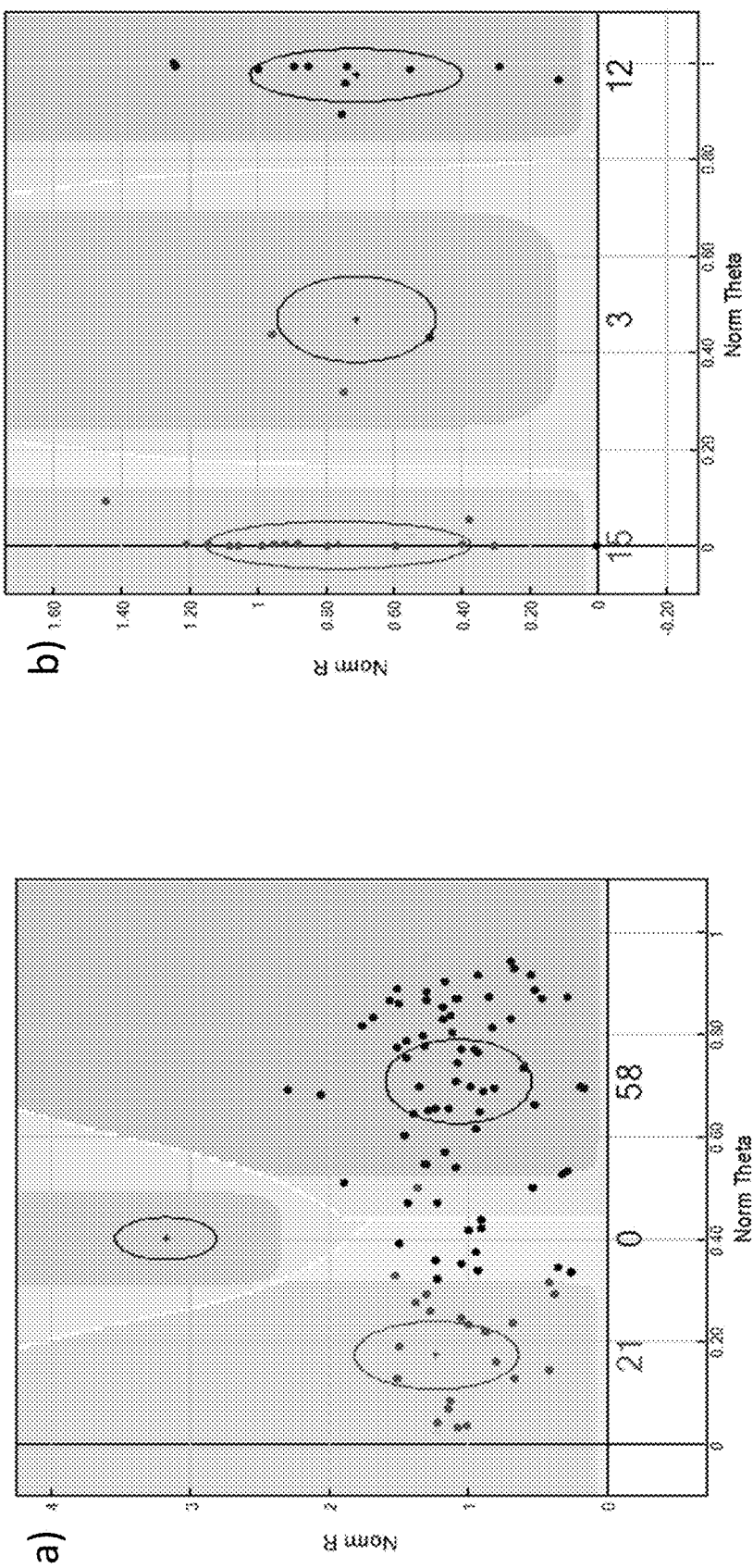

FIG. 15 compares the ILLUMINA® GOLDENGATE® Genotyping Assay using DNA obtained from a) conventional CTAB DNA extraction method using multiple seeds and b) SBEADEX® DNA extraction method using one seed (with tissue wash) followed by the whole genome amplification.

Figure 16:
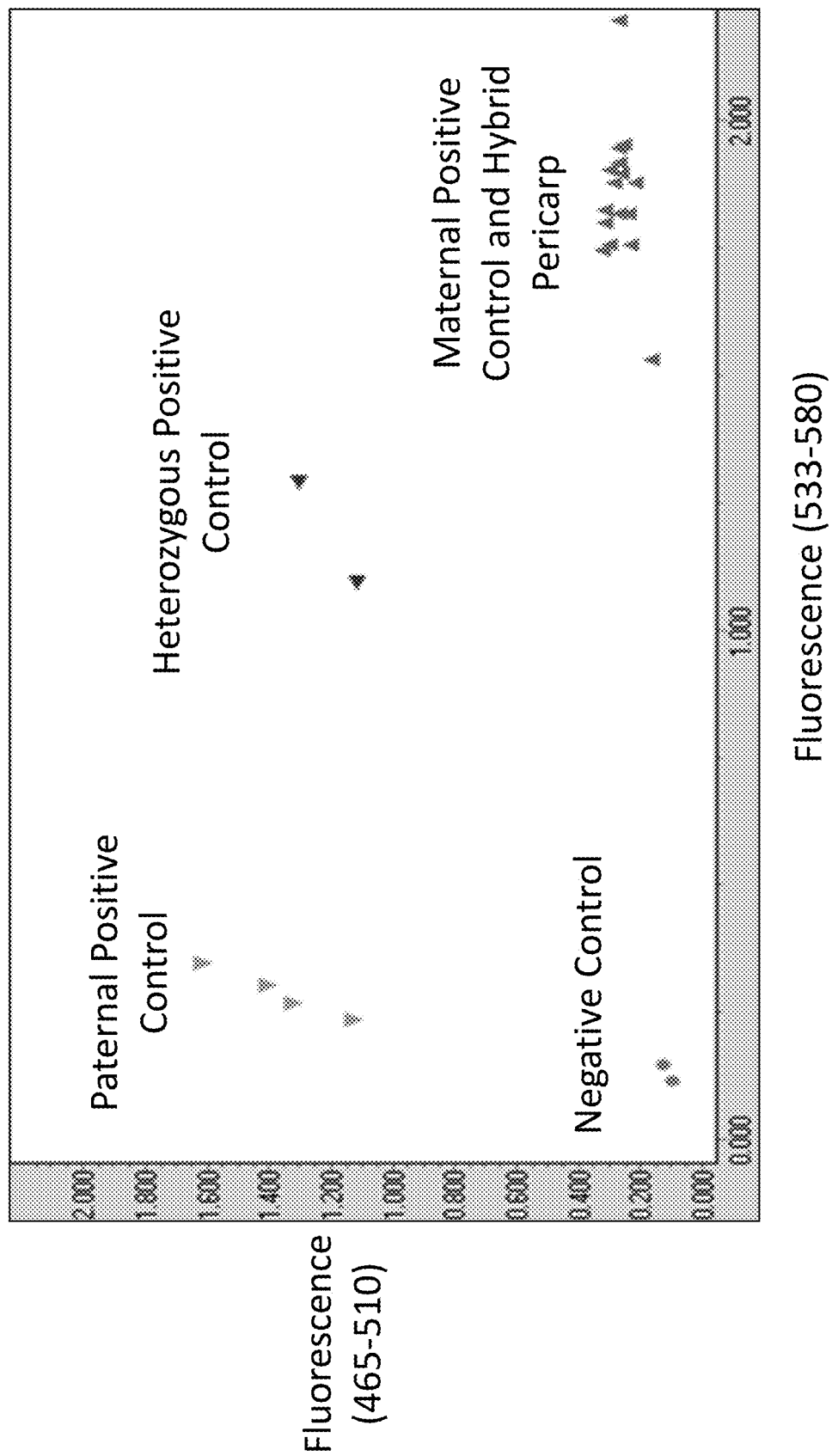

FIG. 16 demonstrates that quality fluorescent marker data can be obtained from a single pericarp.

Figure 17:
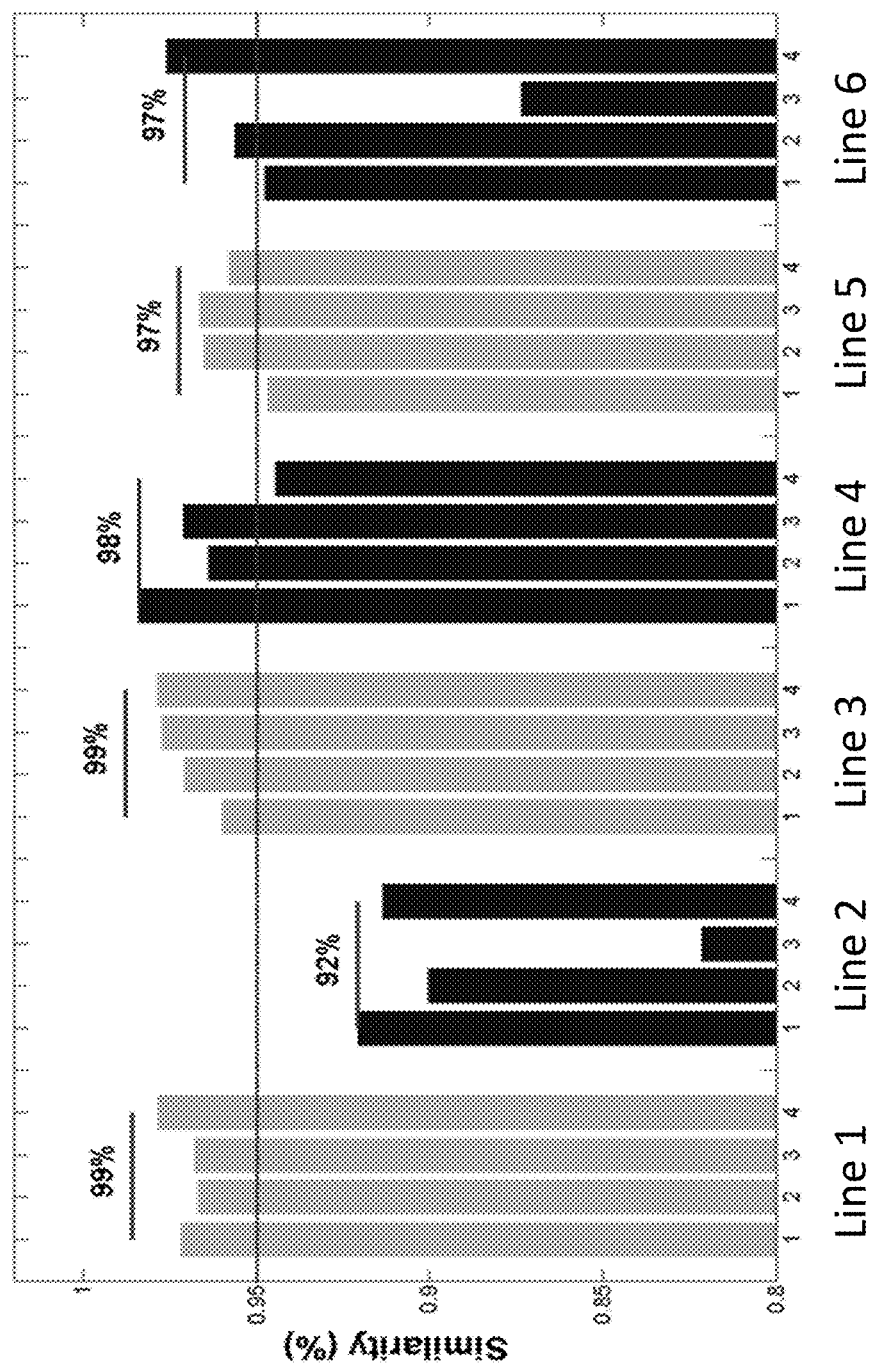

FIG. 17 demonstrates the high degree of similarity between the measured genotype of the pericarp tissue extracted from a single seed (each line) and the known maternal genotype.

DETAILED DESCRIPTION OF PREFERRED EMBODIMENTS

Genotyping of embryos or other seed parts permits molecular characterization early in plant development, allowing selections of a desired genotype to be made weeks or months earlier than other methods such as with phenotyping or plant genotyping. Consequently, resources can be focused earlier on embryos that have the highest probability of developing into desirable plants. Techniques for genetically characterizing seed tissue can greatly enhance a molecular breeding program and eliminate a great deal of effort and resources by allowing breeders to only grow plants with the desired genetics. Furthermore, the ability to reliably genetically characterize an embryo without impeding its ability to germinate, particularly in an immature embryo, can substantially reduce the amount of time required between generations of plants.

Non-destructive genotyping in a plant breeding program may require one or more of the following steps:
1. Separating viable plant sources from other plant material;
2. Preserving the viable plant sources;
3. Obtaining genetic material corresponding to multiple viable plant sources while maintaining the viability of the multiple viable plant sources;
4. Obtaining genetic material for molecular characterization;
5. Molecularly characterizing the genetic material from the multiple viable plant sources;
6. Selecting one or more viable plant sources based on molecular characterizations; and
7. Growing the selected viable plant sources.

The viable plant sources may be seeds, plant embryos, plant tissue, or whole plants, for example. Most typically, viable plant sources are capable of being grown into plants, although not necessarily. The genetic material may be crude, i.e., mixed with other portions of plant tissue including cellulosic and protein materials, or it may be purified (such as, for example, by DNA extraction methods known to one of ordinary skill in the art). The genetic material may be taken directly from the viable plant sources, or it may be taken from other plant material. The preserving step may include keeping the viable plant sources in a manner that preserves an ability to be grown into a plant. The preserving step may include keeping the viable plant sources in a manner that prevents germination. The molecularly characterizing step may involve genotyping, genetic sequencing, RNA sequencing, restriction fragment length polymorphism marker detection, single nucleotide polymorphism detection, whole genome amplification, specific protein detection, oil content measurement, protein content measurement, or any other molecular analysis that may serve as a basis to select or reject particular viable plant sources. The growing step may involve any means of growing plants, including planting in a field or a greenhouse, growing hydroponically, growing aeroponically, or any other method of growing a plant. In some embodiments, the plant is grown to maturity and produces pollen and/or seeds. In some embodiments, one or more of the steps is automated.

Separating Viable Plant Sources.

In one embodiment involving corn, the caps of corn kernels are sliced off while they are still attached to the corn cob. The caps of the corn kernels are typically the farthest part of the kernel from the embryo, which is closer to the tip of the kernel, which is attached to the cob. Each embryo may then be removed, for example, using a small spatula or any other suitable device. In one embodiment, this process is automated using a robot cap slicer, a robotically manipulated spatula, and a machine vision platform for precise cutting and embryo removal control.

In another embodiment, corn kernels may be removed from the cob before embryo removal. The kernels may then be oriented in the same way, for example, by floating the kernels in water or in a solution. The kernels may then be immobilized, while preserving their orientations, for example, by draining them into a container with multiple wells, each well holding an oriented kernel. Small pieces of the tips of the kernels may then be removed; preferably small enough pieces of the tip of the kernels are removed to avoid damaging the embryos. The embryos may then be extracted by gently squeezing the kernels from the cap sides of the kernels.

Following embryo removal, each embryo may be placed in a container with multiple wells, wherein the location of each embryo in each well is recorded, associated, or correlated with the location of genetic material obtained in a subsequent step.

Preserving the Viable Plant Sources

When the viable plant sources are seeds, preservation of seeds for the quantity of time required to perform a molecular analysis typically requires no particular care. When the viable plant sources are embryos, however, special care should be taken to preserve viability. Embryos may be stored in a multiple well plate, where each well corresponds to a well in which extracted tissue to be tested is placed.

In one preferred method, embryos are suspended in an aqueous solution surrounded by a matrix of one or more oils. Oil having a density less than water will cover the embryo(s) in the aqueous solution, while oil having a density greater than water will support the embryo(s) in the aqueous solution. In some embodiments, the one or more embryos is suspended in an aqueous solution surrounded by a matrix of two or more oils, wherein at least one of the two or more oils is more dense than the aqueous solution and at least one of the two or more oils is less dense than the aqueous solution, further wherein the aqueous solution is surrounded by the oil that is more dense than the aqueous solution and the oil that is less dense than the aqueous solution. In some embodiments, antimicrobial agents and/or minimal growth media may be added to the aqueous solution. In some embodiments, the embryos may be stored in cold and/or dark conditions to prevent premature germination. In a preferred embodiment, the embryos are stored at a temperature of approximately 4° C. In some embodiments, the embryos may be transferred for continued storage. In other embodiments, the embryos may be transferred to germination medium, and the embryos may be germinated. In a preferred embodiment, an aliquot of the aqueous solution may be removed; genetic material may be obtained from cellular material in the aliquot; and the genetic material may be used for molecular analysis (e.g. to genotype the stored embryos).

High density oil that may be used in this method includes but is not limited to perfluoro compounds having 12 compounds (e.g., DuPont's lower viscosity KRYTOX® oils). Low density oil that may be used in this method includes but is not limited to phenylmethylpolysiloxane. Other non-toxic oils known to those of ordinary skill in the art may be used instead of or in combination with these compounds.

Obtaining Genetic Material.

The invention includes many different options for the step of obtaining genetic material (e.g. DNA). Genetic material may be obtained from any "shed cellular material", which refers to any plant material remaining after the separation of viable plant sources. Shed cellular material may include embryo and/or endosperm material. If genetic information for the parent plant is desired, genetic material may be obtained from the pericarp.

In one embodiment, a small piece of the scutellum may be excised using any method known in the art, include cutting with a blade or a laser. Preferably, the piece of the scutellum is small enough so as not to compromise embryo viability. The embryo and corresponding piece of scutellum may then be placed in separate containers with wells, in which the well containing the embryo in the embryo container and the well containing the corresponding scutellum in the scutellum container are correlated such that any information gained from the scutellum is associated with the embryo from which the scutellum tissue was obtained.

In another embodiment, when a spatula (or any other implement or device used to excise a piece of the scutellum) is used to remove the embryo from a seed, the spatula may then be dipped into a well in one container that corresponds to a well in a second container that houses the embryo. Preferably, the spatula is dipped into a well containing an aqueous solution. When the spatula is used to remove the embryo, sufficient quantities of endosperm tissue remain on the spatula (i.e. shed cellular material), and the spatula need not contact the kernel from which the embryo was removed following embryo extraction. The spatula may be dipped in the well containing aqueous solution immediately after the embryo has been removed. If the same spatula is used for the removal of multiple embryos and/or endosperm tissue, it preferably will be cleaned between each use to remove any genetic material that could lead to contamination.

In another embodiment, the embryo may be washed, for example with water, to remove any endosperm attached to the embryo. The washed embryo may then be immersed in fresh water or other aqueous solution and agitated to remove a small number of embryo cells from the embryo into the fresh water or other aqueous solution (i.e. shed cellular material). The embryo may then be transferred to a container with multiple wells, and some or all of the fresh water or aqueous solution containing the small number of embryo cells may be transferred to a correlated well in a separate container with multiple wells.

In another embodiment not necessarily requiring embryo extraction or other separation of viable plant sources, a piece of the outer coat of a corn kernel, the pericarp, may be excised in order to conduct a molecular analysis of the parent plant. In this embodiment, kernels may be soaked in water before making cuts in the pericarp. The back side of the kernel (farthest from the embryo) may be cut with a sharp blade, as shown in FIG. 14a. Preferably, the blade is sterilized after the first cut before outer edge of the kernel may be cut with the sharp blade, starting from one end of the first cut, around the edge of the kernel, and down to the other end of the first cut, as shown in FIG. 14b. Sterilized forceps may be used to peel the pericarp tissue from the kernel as shown in FIG. 14c. While the cut can be made on the front side of the kernel (nearest the embryo), the cut is preferably made on the back side to reduce the possibility that the pericarp will be contaminated with endosperm tissue. To further reduce the possibility of contamination, the pericarp tissue may be washed after it is excised. The pericarp may be placed in the well of a container and the seed from which the pericarp was excised (or the embryo from that seed) may be placed in a corresponding well of a separate container. As will be understood by those of ordinary skill in the art, there are other comparable methods for isolating pericarp tissue, and in some embodiments of the invention, pericarp DNA may be extracted without pericarp removal.

The tissue to be analyzed is preferably associated or correlated with its corresponding viable plant source so that the corresponding viable plant source can be selected based on the results of the tissue analysis.

Obtaining Genetic Material for Molecular Characterization

In order for genetic material to be analyzed, it must be freed from the cell such that it is accessible for molecular analysis. This may involve physical treatments such as exposure to cold-heat or just heat, incubation with enzymes, or even DNA extraction techniques (although it is important to note that extraction is not a necessary step in obtaining DNA for molecular analysis). Essentially any process that disrupts the tissue and breaks open cells, thereby releasing DNA that can be used for molecular characterization, may be used in the methods provided herein.

In some embodiments, DNA may be obtained from the shed cellular material by exposing the shed cellular material to cold-heat or heat, agitating the mixture, and optionally repeating. In other embodiments, DNA may be obtained by incubating shed cellular material with an enzyme; the enzyme may be VISCOZYME® L, a multi-enzyme complex containing a wide range of carbohydrases, including arabanase, cellulase, β-glucanase, hemicellulase, and xylanase. (See the Sigma Aldrich product catalog). In still other embodiments, obtaining DNA may comprise extraction of the DNA, such as through the use of magnetic particles that bind genetic material or any method known to one of ordinary skill in the art. However, extraction is not necessary for obtaining DNA.

In other embodiments involving maternal seed tissue such as pericarp tissue, tissue may be dissociated using a cell dissociator (such as gentleMACS™, Miltenyi Biotec), optionally followed by DNA extraction. In another embodiment, the maternal seed tissue may be disrupted in liquid nitrogen prior to DNA extraction. In yet another embodiment, DNA may be extracted directly from washed maternal seed tissue (e.g. using Extract-N-Amp™).

Molecularly Characterizing the Genetic Material from the Multiple Viable Plant Sources In cases where the yield of DNA obtained from embryo tissue is not sufficient for some molecular analysis (e.g. high density genotyping), whole genome amplification techniques may be used. The Qiagen REPLI-g kit, the Sigma-Aldrich SeqPlex kit, or any other technique known to one of ordinary skill in the art may be used to amplify DNA from embryo tissue.

Other useful molecular characterizations may involve sequencing all or part of the genome of the tissue extracted from the seed, or using molecular markers and fluorescent probes to genotype. Molecular characterization need not focus on the genotype of the extracted tissue, but instead may measure other properties such as oil content, oil composition, protein content, or the presence or absence of particular molecules in the tissue.

In a preferred embodiment, genetic material is placed in a well of a multiple well plate containing a bilayer of oil, one layer having a density greater than water and one layer having a density less than water. Multiple wells contain multiple different genetic materials. Fluorescently labeled probes are added to the genetic materials, and thermocycling to cause amplification and hybridization of the probes is performed in the multiple well plate. The wells are irradiated and fluorescence is detected from the labels to generate genotypic data. Alternatively, the genetic material may be sequenced, in whole or in part, in the multiple well plate.

Selecting One or more Viable Plant Sources Based on Molecular Characterizations

In a molecular breeding program, plants or potential plants are selected to participate in subsequent generations based on their genotype. Typically this involves determining whether the plant has inherited one or more desirable traits indicated by genetic markers whose presence or absence can be determined based on the genotyping. Plant breeders select those plants that have the desired traits to participate in further breeding, to inbreed, or as part of a process to create inbreds through haploid doubling techniques.

Growing the Selected Viable Plant Sources.

Those plants that are selected based on the presence of desirable traits as determined by their genotype may be grown into mature plants, to obtain haploid material to create a double haploid inbred, to breed with itself to create an inbred, or to breed with other plants to improve and diversify germplasm.

In one embodiment, a consensus genotype may be derived by considering genotypic data from multiple tissue specimens obtained from one or more seeds, each tissue specimen being a replicate. In a genotyping experiment that identifies multiple nucleotides across multiple positions in a genome, it is not uncommon for any particular experiment to fail to identify one or more of the nucleotides to be identified. Thus, missing nucleotide identifications for each missing position may be noted for each of the specimens. If a nucleotide identification from only one specimen is available for a particular nucleotide position, then that nucleotide identification is assigned as the consensus data for that position. If two or more nucleotide identifications are available for a particular nucleotide position, then the majority of nucleotide identifications for that position is assigned as the consensus data for that position. If no majority identification exists for a position, that position is assigned as missing data for the consensus genotype. The probabilities for consensus accuracy for a given nucleotide position is given in Table 1 for the cases of 1, 2, 3, and 4 replicates, where f represents the error rate in genotyping (e.g., marker call).

TABLE 1

Probabilities of Consensus Accuracy

| Available Replicates | Same Call (Consensus) | Different Call | Probability |
|---|---|---|---|
| 1 | 1 | 0 | $1-f$ |
| 2 | 2 | 0 | $1-f^2$ |
| 2 | 1 | 1 | 0.5 |
| 3 | 3 | 0 | $1-f^3$ |
| 3 | 2 | 1 | $1-3*(1-f)*f^2$ |
| 4 | 4 | 0 | $1-f^4$ |
| 4 | 3 | 1 | $1-4*(1-f)*f^3$ |
| 4 | 2 | 2 | 0.5 |

While the examples provided here relate to obtaining and genotyping tissues from a monocot, specifically maize, those of ordinary skill in the art would understand how to apply the same or similar methods to other monocots and dicots; the methods may be adapted to any plant. For instance, the plant may include but is not limited to maize, soybean, sunflower, sorghum, canola, wheat, alfalfa, cotton, rice, barley, millet, sugar cane, or switchgrass. Further, the genotyping methods disclosed herein may be used to genotype any plant tissue. The consensus genotyping methods may also be used to generate a consensus genotype for multiple specimens of any genetic material obtained from any source without departing from the steps disclosed.

EXAMPLE 1

Embryo Genotyping

A. Collection of Embryo Material:

Embryos were washed 3 times using 2 mL of sterile water. Embryos were incubated in a tube containing either 10 μL, 20 μL, 50 μL, 75 μL, or 150 μL of sterile water for either 10 minutes, 20 minutes, or overnight. It was found that adequate genotyping data can be obtained with any of the dilution volumes, and that 10 minutes was a sufficient incubation time. All protocols for washing and incubating the embryos were used with all three tissue collection methods described below.

Method 1: The tubes containing the embryos were agitated via tapping 10 times and were then spun down in a tabletop centrifuge for 5 seconds. The water was then removed from each tube for analysis. It was found that this method achieved the best results for genotyping.

Method 2: Embryos were washed 3 times using 2 mL of sterile water. Embryos were incubated in a tube containing 50 μL of sterile water for 10 minutes. The water was then removed from the tube for analysis.

Method 3: Embryos were washed 3 times using 2 mL of sterile water. Embryos were incubated in a tube containing 50 μL of sterile water for 10 minutes. Tubes containing the embryos were agitated via tapping 10 times. The water was then removed from each tube for analysis.

B. Methods to Obtain DNA:

Cold-Heat Shock:

Embryo material obtained using all three methods described above was placed in a −80° C. freezer for 20 min; then placed on a thermocycler at 100° C. for 10 min and pipetted up and down to mix. The process was repeated for a total of two rounds. The resulting mixtures were stored at −20° C. It was found that the best results for genotyping were achieved from DNA obtained using this method.

Heat Shock Only:

Embryo tissues were placed on a thermocycler at 100° C. for 10 min and pipetted up and down to mix. The process was repeated for a total of two rounds. The mixtures were stored at −20° C.

Enzymatic Method:

The mixtures from the preceding step were incubated in a 95° C. oven to evaporate off the remaining water. 18.0 μL of PBS solution and 2.0 μL of diluted VISCOZYME® L (commercially available from Sigma-Aldrich; diluted 1:200 in PBS Solution pH 7.4; total vol. 20 μL) were added and the mixtures were incubate at 37° C. for 2 hours. A quantity of 2.0 μL of diluted proteinase K (commercially available from Sigma-Aldrich; diluted 1:20 in PBS Solution pH 7.4) was added and the mixtures were incubated at 55° C. for 50 minutes then heated to 95° C. for 10 min. The mixtures were stored at −20° C.

DNA Extraction:

The mixtures from the methods of Example 1B were incubated in a 95° C. oven to evaporate off the remaining water. 45 μL Lysis buffer PN (LGC Genomics) was added to each mixture, each of which was centrifuged briefly and incubated at 65° C. for 1 hour. To new tubes were added 60 μL Binding buffer PN, 5 μL Sbeadex particles (magnetic particles that bind genetic material, which are commercially available from LGC Genomics) followed by the lysate mixtures, which were then incubated at room temperature for 4 minutes to allow binding of DNA to the particles, vortexed briefly and placed in a magnetic rack to concentrate beads. The lysis buffer was removed and 100 μL wash buffer PN1 (LGC Genomics) was added to resuspend the beads. Washing was repeated using 100 μL wash buffer PN2 (LGC Genomics) followed by a 100 μL pure water wash. 10 μL elution buffer PN was added and the mixtures were incubated at 55° C. for 10 minutes with vortexing every 3 minutes. The magnetic rack was used to concentrate beads and the eluate was transferred to new tubes and stored at −20° C.

C. Whole Genome Amplification

When whole genome amplification was required the following protocol was followed using the REPLI-g® Single Cell Kit (commercially available from Qiagen). Whole genome amplification was done to achieve higher DNA yield and to facilitate the detection of high density marker sets.

2.5 μL template DNA was combined with 2.5 μL Buffer D1 (commercially available from Qiagen; total volume 5.0 μL) and incubated at room temperature for 3 minutes. 5.0 μL Buffer N1 (commercially available from Qiagen; total volume 10.0 μL) was added and the mixtures were vortexed and centrifuged briefly. A Master Mix containing 9.0 μL nuclease-free water, 29.0 μL REPLI-g® Reaction Buffer (commercially available from Qiagen) and 2.0 μL REPLI-g® DNA Polymerase (commercially available from Qiagen) was used per reaction to give 50.0 μL total volume. The mixtures were run on a thermocycler using a 30° C. for 8 hours and 4° C. thereafter. DNA quantitation was performed using a Qubit assay (commercially available from Life Technologies). The DNA product was used directly in the genotyping step.

D. Molecular Analysis

TAQMAN® Marker Analysis

Marker analysis was carried out using TAQMAN® assays (commercially available from Life Technologies). DNA was diluted to a target concentration of 20 ng/μL. A 384 plate containing the DNA was loaded into LC480 real-time PCR thermocycler and run using the following program: preincubation: 1 cycle (95° C. for 5 minutes); amplification: 45 cycles, (−95° C. for 30 seconds, −60° C. for 45 seconds (single acquisition), −72° C. for 1 minute (single acquisition); cooling: 1 cycle, (−72° C. for 10 minutes, −40° C. for 30 seconds). Calls were read using Roche LC480 LightCycler® Software (commercially available from Roche Diagnostics).

Results

Figure 1:
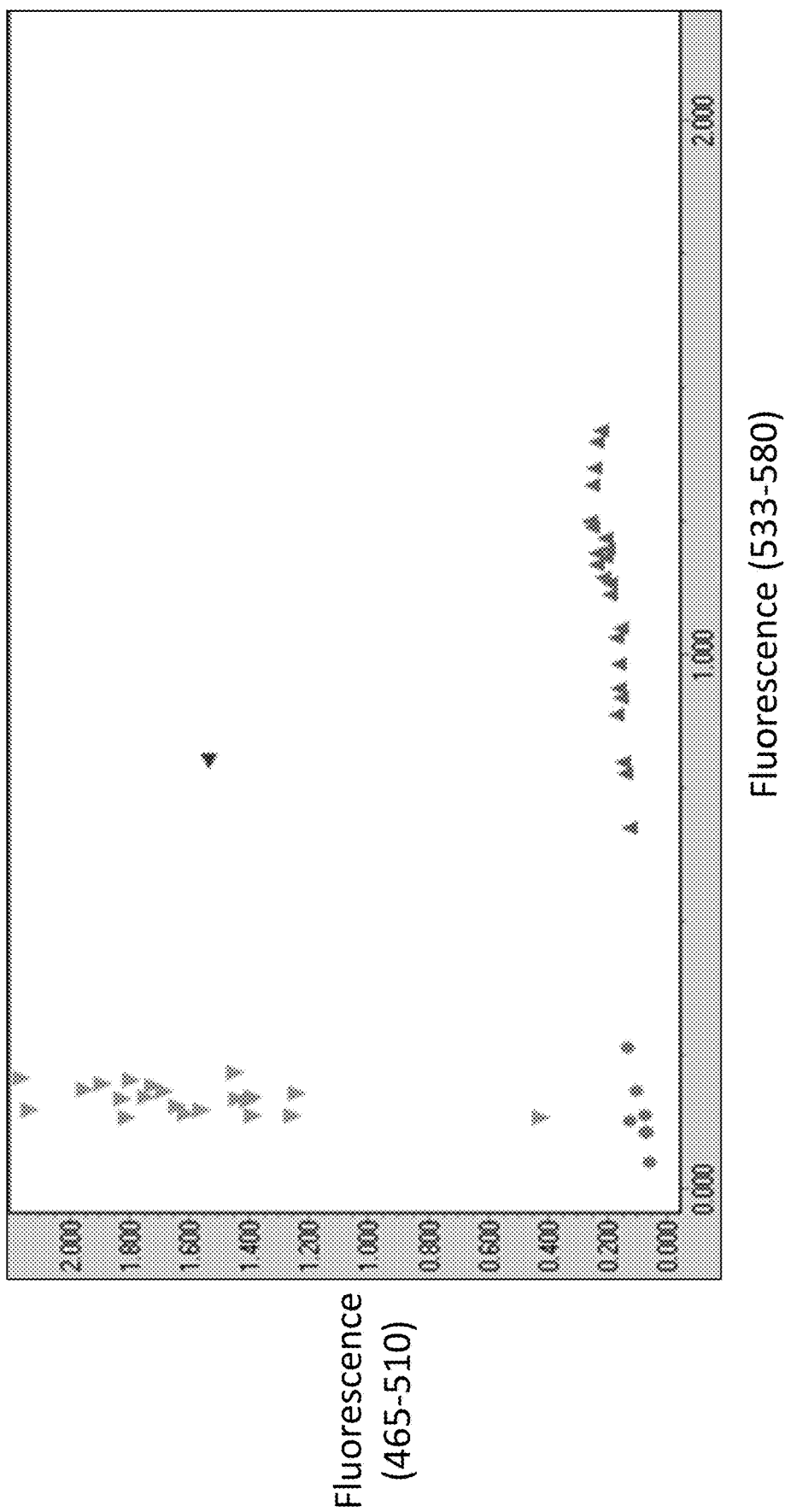
FIG. 1 depicts genotyping data from one marker using DNA obtained with the cold-heat shock treatment. The data represents three different treatments (incubate only; incubate and tap; and incubate, tap, and spin) in each of four different incubation volumes (10 µL, 20 µL, 50 µL, and 75 µL).
Figure 2:
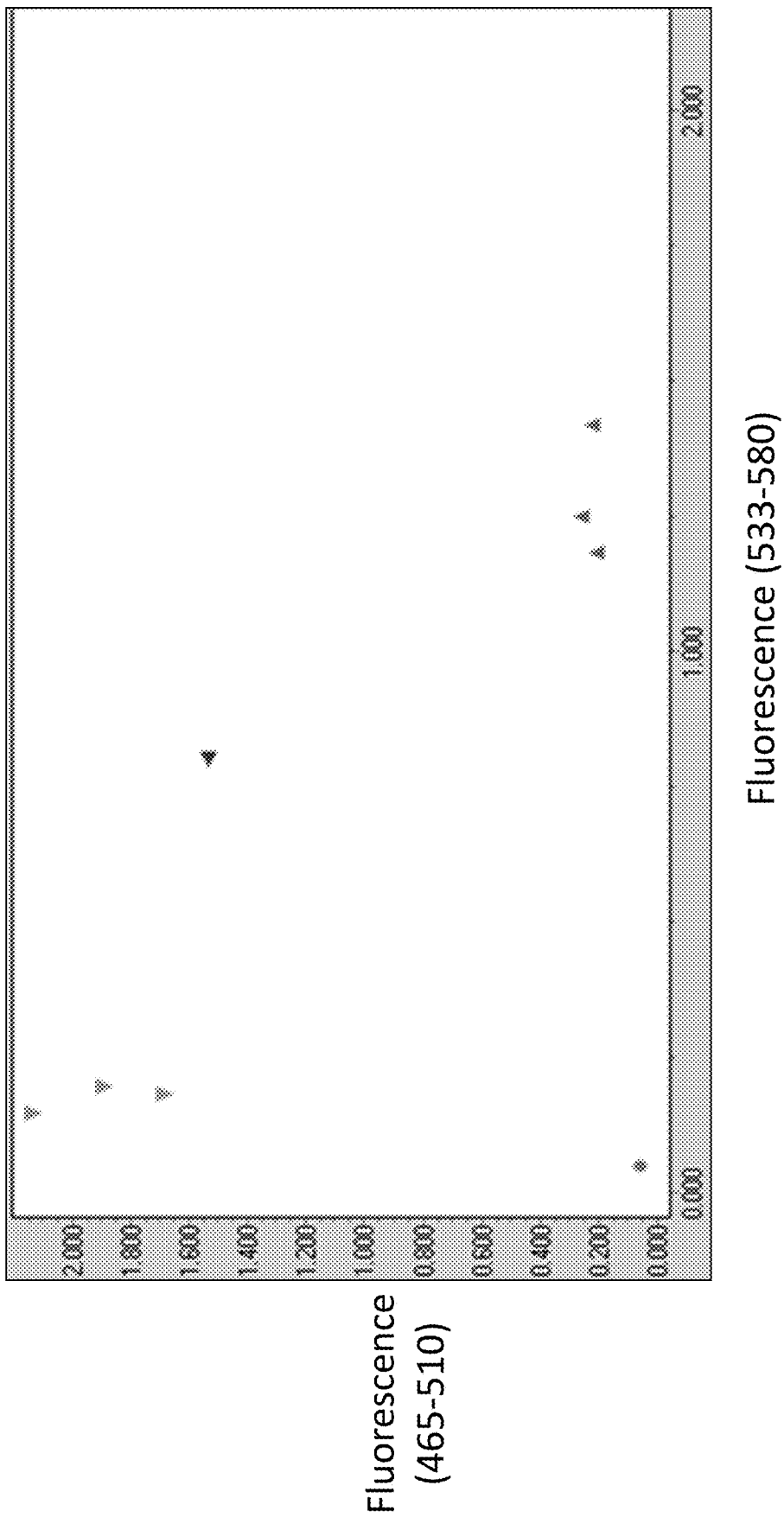
FIG. 2 depicts genotyping data from one marker using DNA obtained with the cold-heat shock treatment. The data represents one treatment (incubate, tap, and spin) in an incubation volume of 50 µL.
Figure 3:
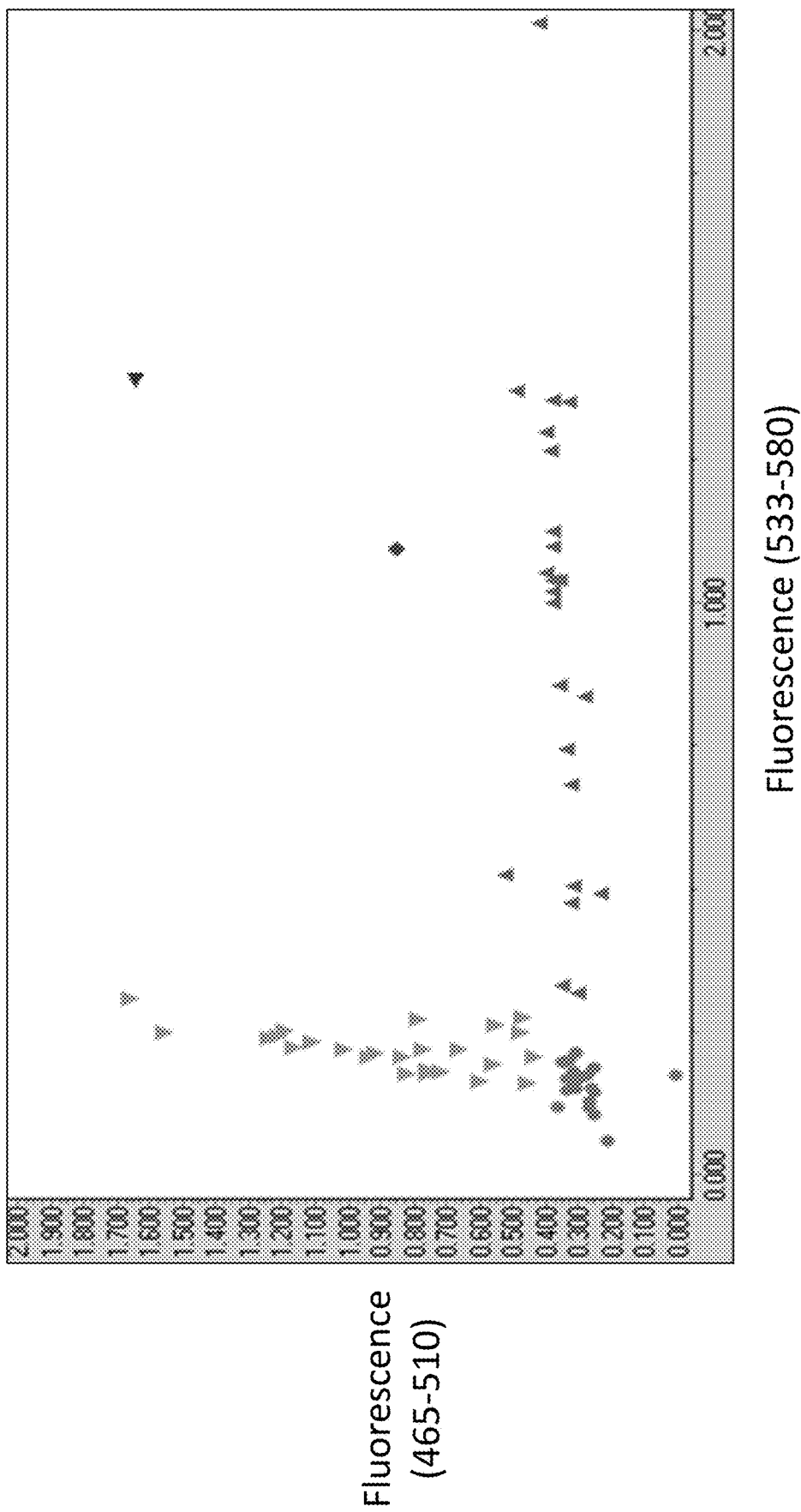
FIG. 3 depicts genotyping data from one marker using DNA obtained from cold-heat shock, heat shock, incubation with VISCOZYME® L, or DNA extraction using the Sbeadex method. The data represents three different treatments (incubate only; incubate and tap; and incubate, tap, and spin) in an incubation volume of 50 µL.
Figure 4:
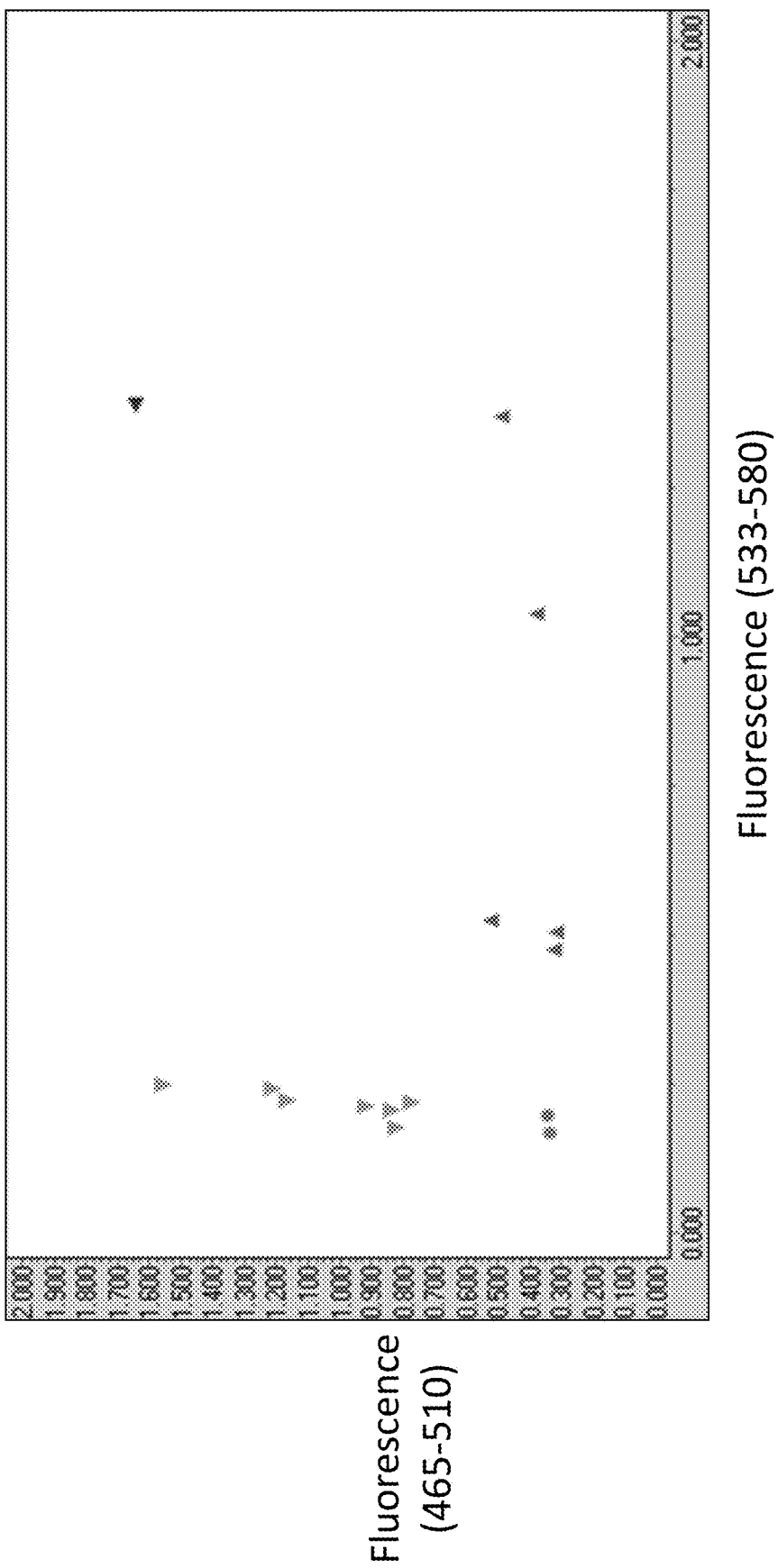
FIG. 4 depicts genotyping data from one marker using DNA obtained with the cold-heat shock treatment. The data represents one treatment (incubate, tap, and spin) in an incubation volume of 50 µL.
Figure 5:
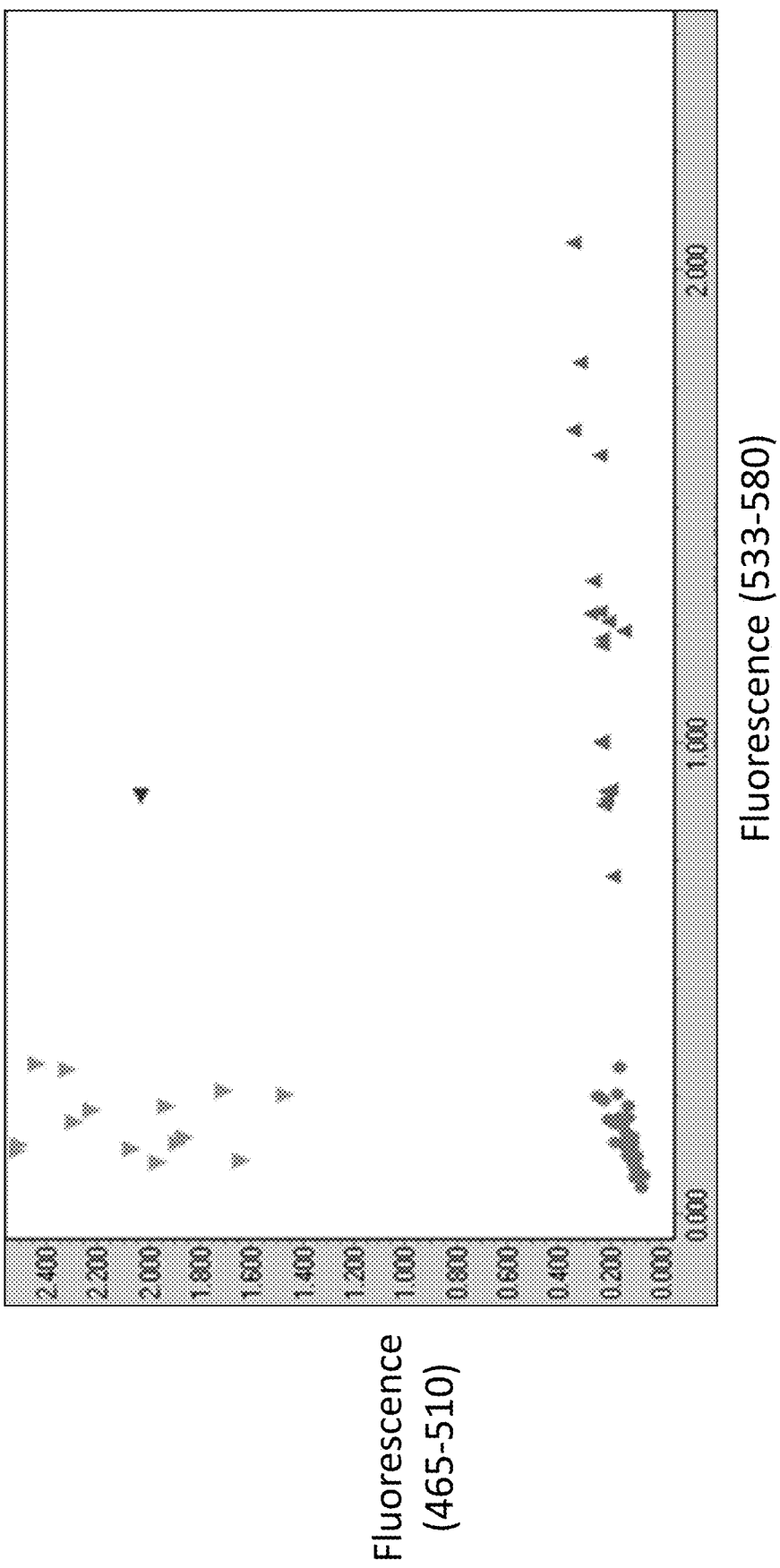
FIG. 5 depicts genotyping data from one marker using DNA obtained from cold-heat shock, incubation with VISCOZYME® L, or DNA extraction using the Sbeadex method. The data represents three different treatments (incubate only; incubate and tap; and incubate, tap, and spin), each in an incubation volume of 50 µL.
Figure 6:
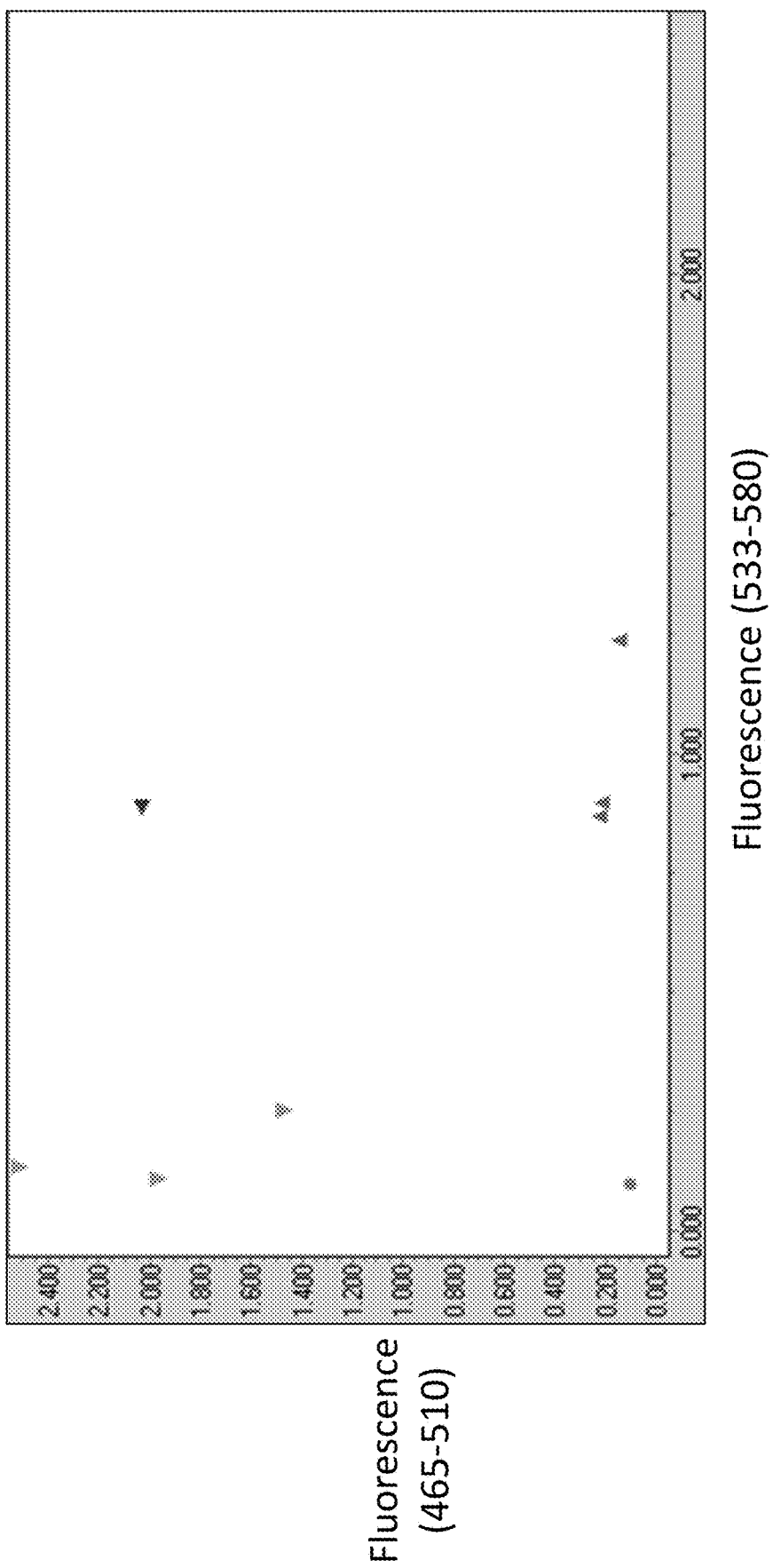
FIG. 6 depicts genotyping data from one marker using DNA obtained with the cold-heat shock treatment. The data represents one treatment (incubate, tap, and spin) in an incubation volume of 50 µL.
Figure 7:
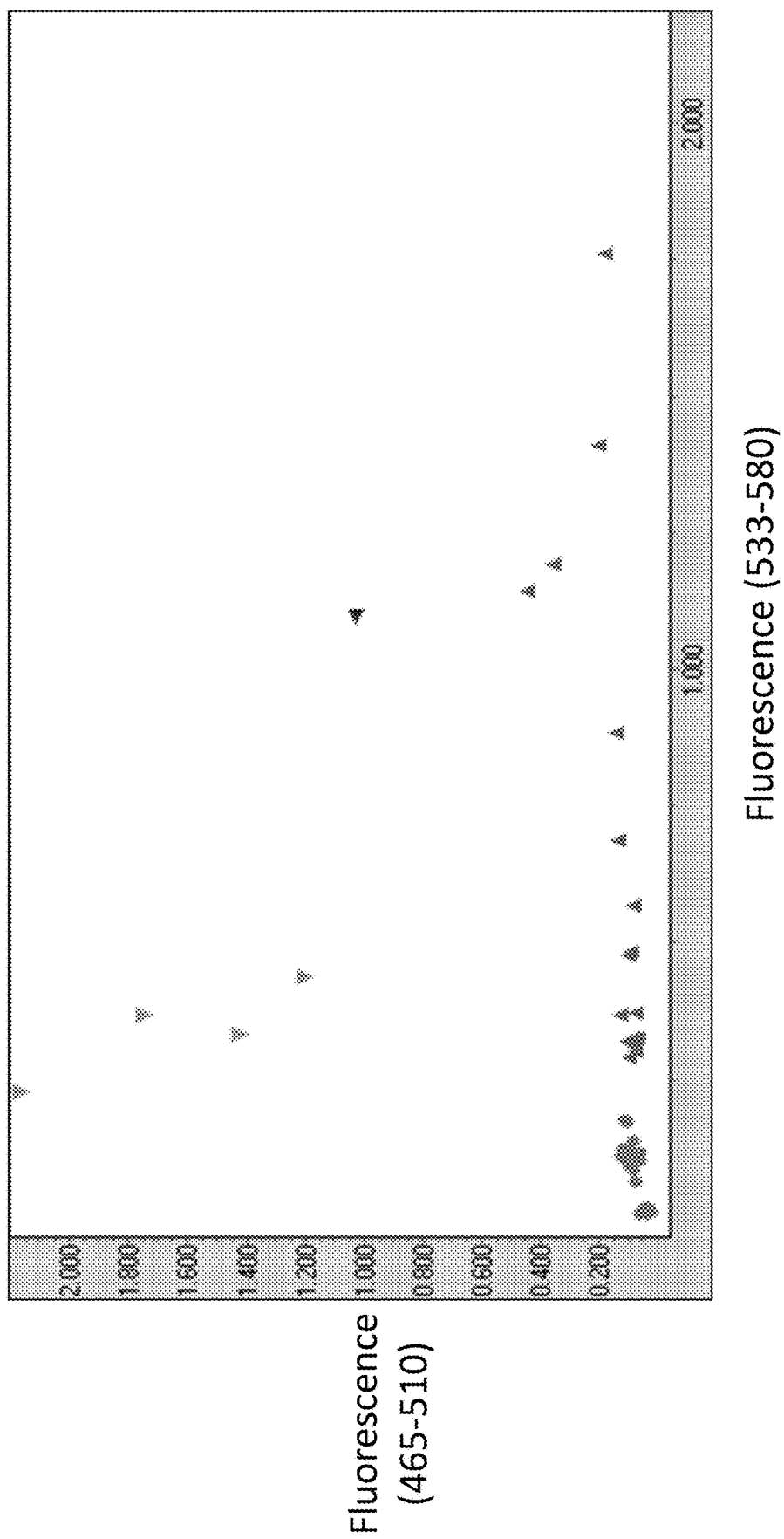
FIG. 7 depicts genotyping data from one marker using DNA obtained with the cold-heat shock treatment. The data represents three treatments (incubate only; incubate and tap; and incubate, tap, and spin), each in an incubation volume of 150 µL.
Figure 8:
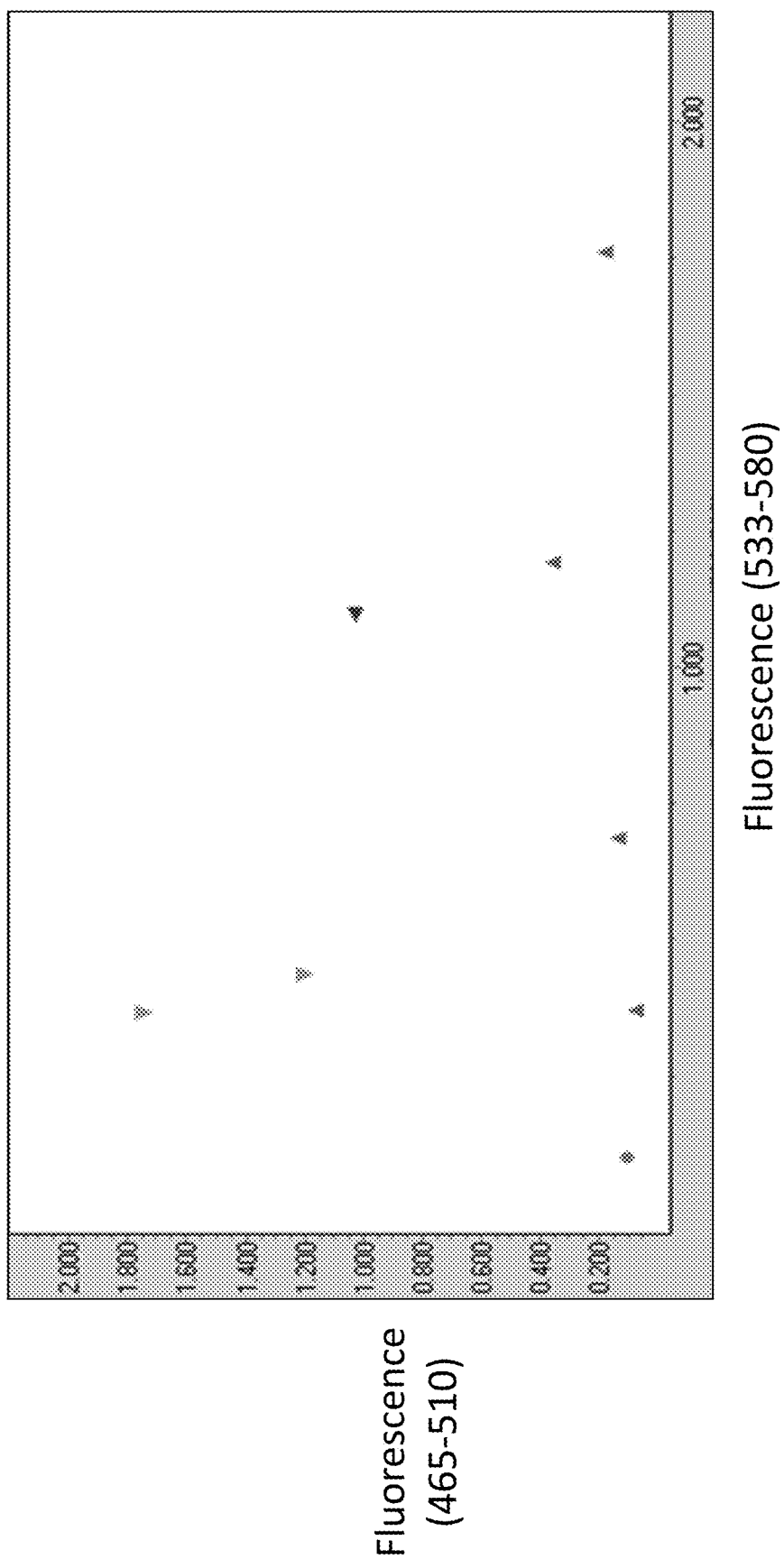
FIG. 8 depicts genotyping data from one marker using DNA obtained with the cold-heat shock treatment. The data represents one treatment (incubate, tap, and spin) in an incubation volume of 150 µL.
Figure 9:
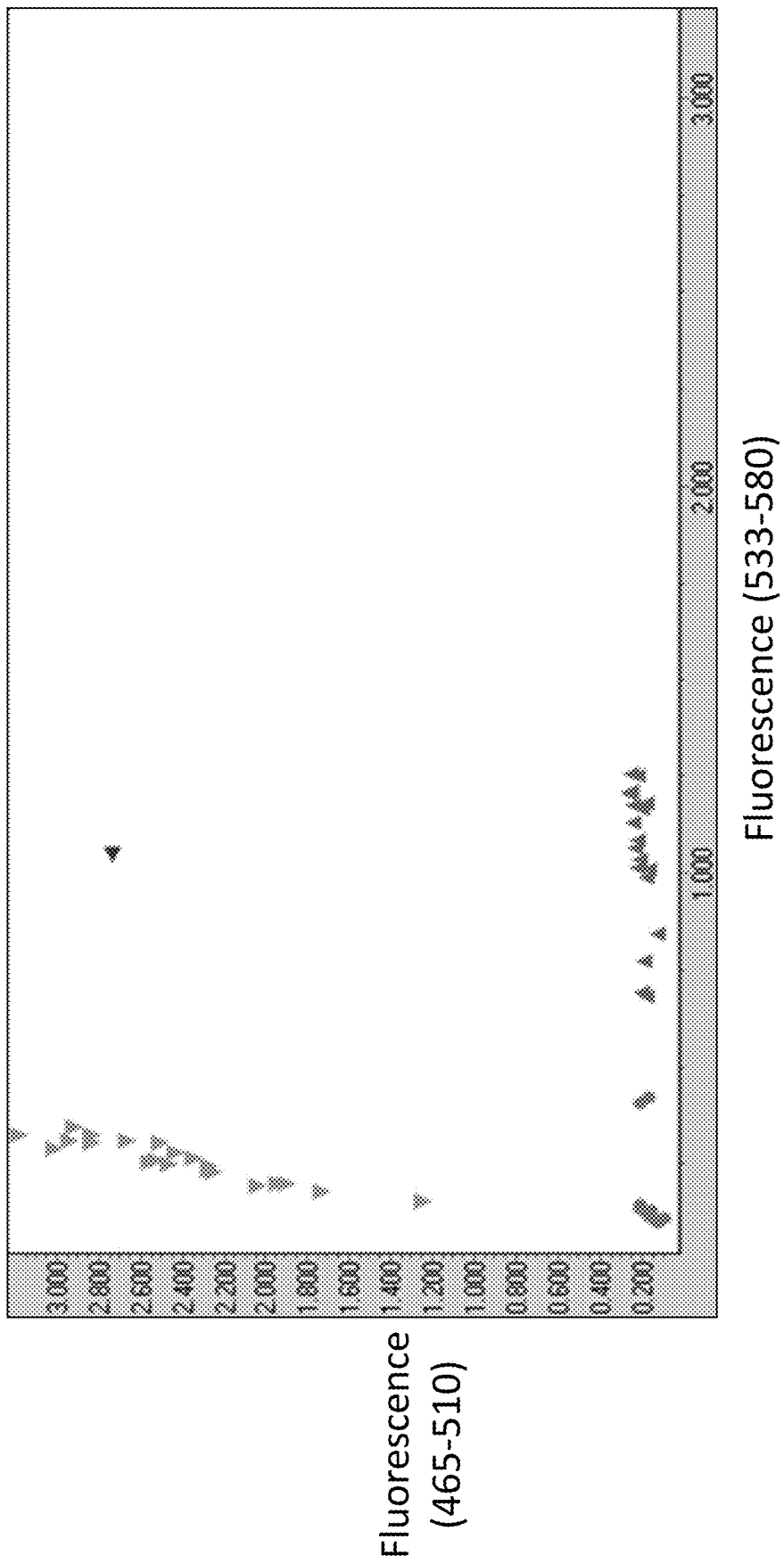
FIG. 9 depicts genotyping data from one marker using DNA obtained with the cold-heat shock treatment or no treatment at all following washing of the shed cellular material. The data represents three treatments (incubate only; incubate and tap; and incubate, tap, and spin) each in one of two incubation volumes (50 µL and 100 µL).
Figure 10:
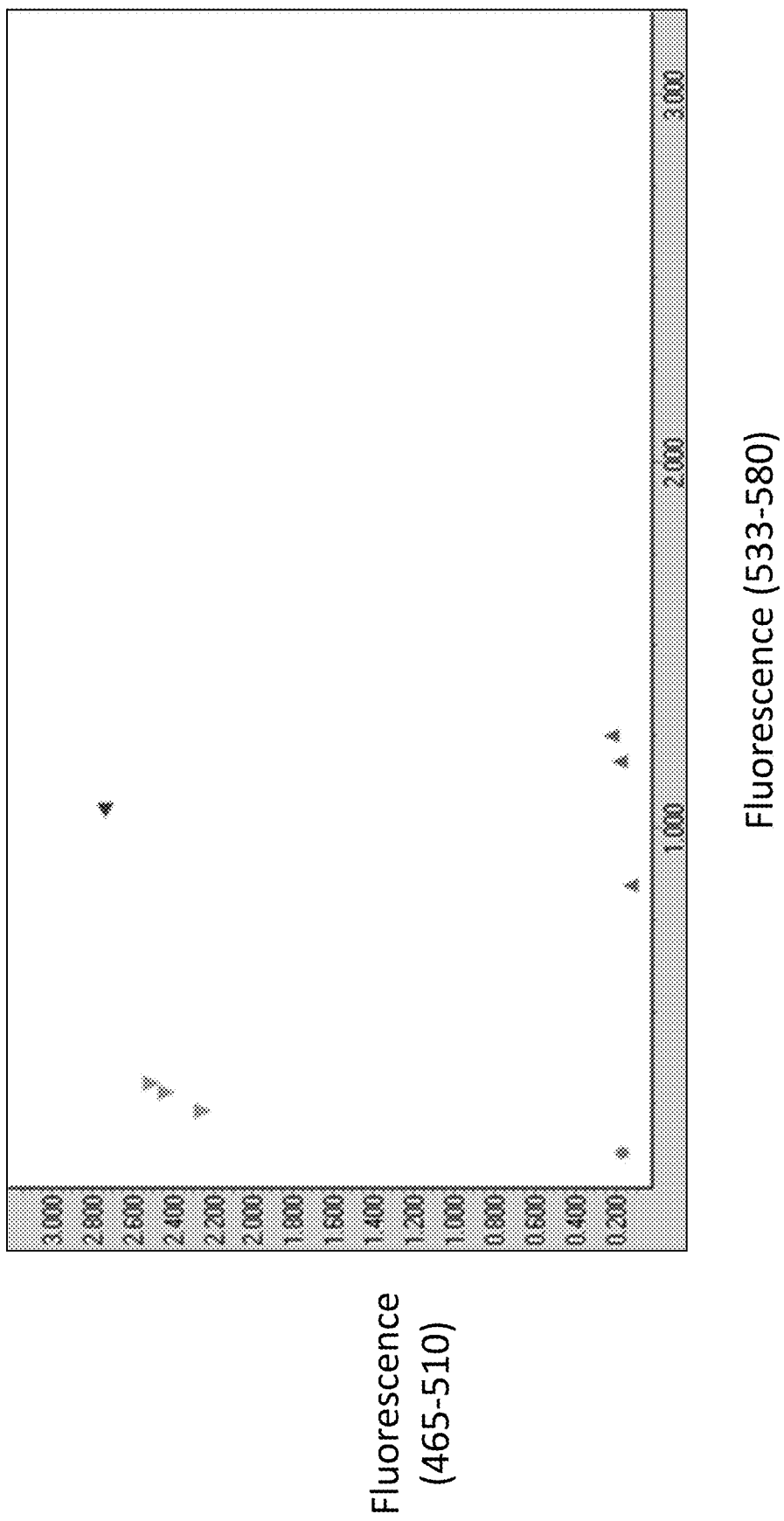
FIG. 10 depicts genotyping data from one marker using DNA obtained with the cold-heat shock treatment. The data represents one treatment (incubate, tap, and spin) in an incubation volume of 50 µL.

The foregoing methods all gave acceptable genotyping results. Genotypic data is shown in FIGS. 1-11, which include data from all permutations of the methods disclosed in this example. FIG. 1 depicts genotyping data from one marker using DNA obtained with the cold-heat shock treatment. The data represents three different treatments (incubate only; incubate and tap; and incubate, tap, and spin) in each of four different incubation volumes (10 µL, 20 µL, 50 µL, and 75 µL). FIG. 2 depicts genotyping data from one marker using DNA obtained with the cold-heat shock treatment. The data represents one treatment (incubate, tap, and spin) in an incubation volume of 50 µL. FIG. 3 depicts genotyping data from one marker using DNA obtained from cold-heat shock, heat shock, incubation with VISCO-ZYME® L, or DNA extraction using the Sbeadex method. The data represents three different treatments (incubate only; incubate and tap; and incubate, tap, and spin), each in an incubation volume of 50 µL. FIG. 4 depicts genotyping data from one marker using DNA obtained with the cold-heat shock treatment. The data represents one treatment (incubate, tap, and spin) in an incubation volume of 50 µL. FIG. 5 depicts genotyping data from one marker using DNA obtained from cold-heat shock, incubation with VISCO-ZYME® L, or DNA extraction using the Sbeadex method. The data represents three different treatments (incubate only; incubate and tap; and incubate, tap, and spin), each in an incubation volume of 50 µL. FIG. 6 depicts genotyping data from one marker using DNA obtained with the cold-heat shock treatment. The data represents one treatment (incubate, tap, and spin) in an incubation volume of 50 µL. FIG. 7 depicts genotyping data from one marker using DNA obtained with the cold-heat shock treatment. The data represents three treatments (incubate only; incubate and tap; and incubate, tap, and spin), each in an incubation volume of 150 µL. FIG. 8 depicts genotyping data from one marker using DNA obtained with the cold-heat shock treatment. The data represents one treatment (incubate, tap, and spin) in an incubation volume of 150 µL. One of the homozygous calls was incorrect. FIG. 9 depicts genotyping data from one marker using DNA obtained with the cold-heat shock treatment or no treatment at all following washing of the shed cellular material. The data represents three treatments (incubate only; incubate and tap; and incubate, tap, and spin), each in one of two incubation volumes (50 µL and 100 µL). FIG. 10 depicts genotyping data from one marker using DNA obtained with the cold-heat shock treatment. The data represents one treatment (incubate, tap, and spin) in an incubation volume of 50 µL. FIG. 11 depicts genotyping data from one marker using DNA obtained with the cold-heat shock treatment and whole genome amplification (using the REPLI-g Single Cell Kit) to obtain sufficient yield of DNA prior to genotyping. The data represents four treatments (incubate only; vortex at speed 3 for 5 seconds; vortex at speed 10 for 5 seconds; and vortex at speed 10 for 30 seconds) in an incubation volume of 10 µL.

EXAMPLE 2

Embryo Storage

Two lines of maize germplasm were selected for testing the impacts of extended embryo storage in an oil matrix on germination rates. Embryos from each line were isolated by hand before being placed into their respective storage condition. All embryos were plated on germination media to evaluate germination rates in a controlled growth chamber. Six embryos of each line were immediately plated on germination media without any storage exposure to act as a control for germination in a controlled growth chamber. Seventy two (72) embryos of each line were isolated and evenly divided across three storage conditions, with a dedicated storage tube for each embryo:

Storage condition 1: 24 embryos were placed in 50 µL aqueous solution surrounded by two layers of oil with significantly different densities, one with a density significantly greater than water and one with a density significantly less than water.

Storage condition 2: 24 embryos were placed in a 50 uL droplet of aqueous solution with an added antimicrobial agent, surrounded by the two oils of condition 1.

Storage condition 3: 24 embryos were placed in a 50 uL droplet of minimal growth media with an added antimicrobial agent, surrounded by the two oils of condition 1.

All tubes were placed in a dark refrigerator at 4 degrees centigrade for the duration of the experiment. At four (4) time points, 6 embryos of each line were removed from their storage condition and plated on germination media in a controlled growth chamber to evaluate germination rates. The time points were as follows:

Time point 1: 15 minutes after placement into storage.
Time point 2: 1 day after placement into storage.
Time point 3: 5 days after placement into storage.
Time point 4: 10 days after placement into storage.

Embryo germination rates were then monitored to determine optimal storage conditions. The results of these tests are shown in FIGS. 12 and 13 (results for two different lines of maize). It was found that germination rates were excellent in each of the three storage methods.

EXAMPLE 3

Pericarp Genotyping

A. Pericarp Peeling

Kernels of corn were removed from the cob and soaked for 60 minutes in deionized water. A scalpel blade was sterilized using a bead sterilizer. The scalpel was used to cut the back side of the seeds (away from the embryo) near the tips, as shown in FIG. 14*a*. The scalpel was again sterilized using a bead sterilizer and cooled in sterile water. The scalpel was then used to cut along the outer edge of the kernel, as shown in FIG. 14*b*. Forceps were sterilized in a bead sterilizer, cooled, then used to peel the pericarp from the kernel, as shown in FIG. 14*c*. The pericarp tissue from each kernel was then placed in microcentrifuge tubes.

B. Pericarp Washing

Three different washing solutions were tested. The best results were achieved washing with 1% sodium dodecyl sulfate (SDS) solution, although adequate results were achievable using water and ethanol. An alternative washing method using sonication also gave adequate results. The washing protocol used began by adding 1 mL wash solution to the microcentrifuge tubes, which was placed in an inverter for 1 minute. The wash solution was removed and replaced with 1 mL fresh wash solution, then the microcentrifuge tubes were again placed in an inverter, this time for 4 minutes. The pericarp tissue was then removed, rinsed with distilled water, and placed into a new microcentrifuge tube. The sonication protocol placed the pericarp tissue in a sonicator for 1 minute. The tissue was then removed, rinsed with distilled water, and placed in a fresh microcentrifuge tube.

C. Obtaining DNA

Five methods for obtaining DNA were tested. The best results were achieved with the gentleMACS™ protocol with water or TE supernatants.

gentleMACS™/Water or TE supernatants: In this method, pericarp tissue was placed directly onto the rotor of a gentleMACS™ M tube. 300 ul of water or TE buffer was added to the tube, which was then closed and placed in a gentleMACS™ machine. The automated program "Protein_01.01" was run. For pericarp tissues that were not fully dissociated, further mixing and running of the automated program was done. Next, the mixtures were spun down in the GentleMACS™ tube and transferred to a new 1.5 ml Eppendorf tube. The Eppendorf tube was then centrifuged at 14000 rpm for 2 minutes, and the supernatant were transferred to a fresh 1.5 ml Eppendorf tube for the molecular analysis. No extraction of DNA was required in this method.

GentleMACS™/SBEADEX®: In this method, pericarp tissue was placed directly onto the rotor of a gentleMACS™ M tube. 300 µL of SBEADEX® Lysis Buffer PN was added to the tube, which was then closed and placed in a gentleMACS™ machine. The automated program "Protein_01.01" was run. For pericarp tissues that were not fully dissociated, further mixing and running of the automated program was done. Next, the mixtures were centrifuged and incubated at 65° C. for 1 hour with occasional agitation. 360 µL of Binding Buffer PN and 30 µL SBEADEX® particles were added to fresh 1.5 mL Eppendorf tubes. The tubes with the pericarp tissue were centrifuged and the lysate was transferred to the fresh tubes. These were then incubated at room temperature for 4 minutes to allow the DNA to bind to the SBEADEX® particles. The tubes were then vortexed briefly then placed in a magnetic rack to concentrate the beads. The lysis buffer was removed and 600 µL of wash buffer PN1 was added to each tube and the beads were resuspended. The tubes were again placed in a magnetic rack to concentrate the beads and the wash buffer PN1 was removed. This washing procedure was repeated using 600 µL of wash buffer PN2, then repeated again using 600 µL of pure water. Following this third washing step, 40 µL of elution buffer PN was added and the tubes were incubated at 55° C. for 20 minutes and vortexed every 3 minutes. A magnetic plate was used to concentrate the beads, and the eluate was transferred into fresh tubes, and then stored at −20° C. until molecular characterization.

gentleMACS™/Extract-N-Amp™: In this method, pericarp tissue was again placed directly onto the rotor of a gentleMACS™ M tube. 300 µL of sterile water was added to the tube, which was then closed and placed in a gentleMACS™ machine. The automated program "Protein_01.01" was run. For pericarp tissues that were not fully dissociated, further mixing and running of the automated program was done. The homogenate was transferred to a 1.5 mL microcentrifuge tube and centrifuged for 1 minute at 10,000 rpm. The supernatant was removed without disturbing the tissue pellet at the bottom of the tube. 30 µL of Extraction Solution/Seed Preparation Solution mix (Sigma-Aldrich Extract-N-Amp™ Seed PCR kit) was added and the resulting mixture was thoroughly mixed. The mixture was transferred to PCR strip tubes for use on the thermocycler, which was programmed to hold 55° C. for 10 minutes, then 95° C. for 3 minutes, then to hold 4° C. indefinitely. 30 µL of Neutralization Solution B was added.

Liquid Nitrogen/SBEADEX®: 1.5 mL microcentrifuge tube pestles were placed in liquid nitrogen to cool. Pericarp tissue was placed in microcentrifuge tubes along with the cooled pestles and the entire tube was placed in liquid nitrogen. Liquid nitrogen was added to the tubes. The pericarp tissue was ground slowly and thoroughly using the pestle. The tubes were occasionally dipped back into the liquid nitrogen to keep the tissue cold. After grinding, 90 µL of Lysis buffer PN was added to each tube, which was then briefly centrifuged then incubated at 65° C. for 1 hour. 120 µL of binding buffer PN and 10 µL of SBEADEX® particles were added to fresh tubes, and the lysate from the grinding step was added to the new tubes. These were then incubated at room temperature for 4 minutes to allow the DNA to bind to the SBEADEX® particles. The mixtures were then briefly vortexed and placed in a magnetic rack to concentrate the beads. The lysis buffer was removed and 200 µL of wash buffer PN1 was added to each tube and the beads were resuspended. The tubes were again placed in a magnetic rack to concentrate the beads and the wash buffer PN1 was removed. This washing procedure was repeated using 200 µL of wash buffer PN2, then repeated again using 200 µL of pure water. Following this third washing step, 20 µL of elution buffer PN was added and the tubes were incubated at 55° C. for 10 minutes and vortexed every 3 minutes. A magnetic plate was used to concentrate the beads, and the eluate was transferred into fresh tubes, and then stored at −20° C. until molecular characterization.

Extract-N-Amp™: A master mix of 18 parts extraction solution and 2 parts of seed preparation solution was made and 20 µL of the solution added to pericarp tissue in 0.2 mL PCR strip tubes. The mixtures were placed in a thermocycler set at 55° C. for 10 minutes, 95° C. for 3 minutes, then 4° C. indefinitely. 20.0 µL of Neutralization Solution B was added and the liquid portion of the mixture was transferred to fresh 1.5 mL microcentrifuge tubes.

D. Molecular Testing

QUBIT® dsDNA HS Assay Kit: QUBIT® reagent was diluted into QUBIT® buffer at a 1:200 ratio to make a working solution. 1 µL of the PCR products of step 2B was transferred to 0.5 mL QUBIT® assay tubes and 199 µL of the working solution. Standards were made by adding 10 µL of standard to 190 µL of QUBIT® working solution. The PCR products and standards were vortexed for 2-3 seconds then briefly centrifuged. The tubes were then incubated at room temperature for 2 minutes. The tubes were then inserted into a QUBIT® 2.0 fluorometer and readings were recorded.

Whole Genome Amplification (Seqplex): The preferred method of whole genome amplification is the Seqplex method using the Seqplex Enhanced DNA Amplification Kit. To 1 µL of each DNA solution generated in step C was added 2 µL library preparation buffer and 11 µL pure water. The solution was centrifuged, vortexed, and centrifuged again, incubated on a thermocycler at 95° C. for 2 minutes, then held at 4° C. After cooling, 1 µL of library preparation enzyme was added. The solution was centrifuged, vortexed, and centrifuged again, then incubated on a thermocycler at 16° C. for 20 minutes, 24° C. for 20 minutes, 37° C. for 20 minutes, 75° C. for 5 minutes, then held at 4° C. The solution was the briefly centrifuged. 15 µL of this solution was added to 15 µL of 5× Amplification Mix (A5112), 1.5 µL DNA Polymerase for SeqPlex, 42.5 µL sterile water, and 1 µL SYBR Green, diluted 1:1000. This solution was mixed thoroughly, and each reaction mix was divided into five 15 µL aliquots on a 384 well plate. The amplification thermocycle began with an initial denaturation at 94° C. for 2 minutes followed a sufficient number of cycles to reach 2-3 cycles into the plateau (typically about 24 cycles): 94° C. denature for 15 seconds, 70° C. anneal/extend for 5 minutes, read fluorescence, repeat. After cycling, the reaction mix was held at 70° C. for 30 minutes then held at 4° C. After cooling, the samples were purified via QIAquick PCR purification.

Whole Genome Amplification (REPLI-g Single Cell Kit): Denaturation buffer D1 was prepared by adding 3.5 µL of reconstituted buffer DLB and 12.5 nuclease-free water. Neutralization buffer N1 was prepared by adding 4.5 µL of stop solution and 25.5 μL of nuclease-free water. 2.5 μL of the denaturation buffer was added to each 2.5 μL aliquot of DNA solution prepared in step C. This solution was incubated at room temperature for 3 minutes. 5.0 μL of the neutralization buffer N1 was added, and the solution was vortexed then centrifuged briefly. Master mix was prepared with 9.0 μL nuclease-free water, 29.0 μL of REPLI-g reaction buffer, and 2.0 μL of REPLI-g DNA polymerase per reaction. 40.0 μL of this master mix was added to each solution, which is then run on a thermocycler at 30° C. for 8 hours, then cooled to 4° C.

The whole genome amplification products were evaluated using the QUBIT® assay to determine yield of DNA.

Genotyping Assays. Both high density markers (the ILLUMINA® 3072X chip) and Taqman marker analysis were successfully employed to genotype the genetic materials described in this example. Data demonstrating the effectiveness of the foregoing techniques is presented in FIGS. 2-4. FIG. 15 compares the data quality obtained using DNA extraction methods against that obtained using whole genome amplification. While both methods give acceptable results, the whole genome amplification method gives preferable results, with each of the three haplotypes well-resolved. FIG. 16 is a fluorescent marker scatter plot demonstrating that quality fluorescent marker data can be obtained from a single pericarp tissue sample. In fact, the methods of the invention allow genotyping using many markers, tens or potentially hundreds, using pericarp tissue extracted from a single seed. FIG. 17 demonstrates the reliability of the methods of the invention because of the high degree of similarity between the measured genotype of the pericarp tissue extracted from a single seed (each line) and the known maternal genotype.

We claim:

1. A method for performing molecular analysis of one or more plant embryos comprising agitating the plant embryos to remove cellular material for molecular analysis, storing the one or more plant embryos in an aqueous solution surrounded by a matrix of at least two oils, wherein one of the at least two oils is more dense than the aqueous solution and one of the at least two oils is less dense than the aqueous solution, obtaining genetic material from the cellular material removed from the plant embryos, and performing molecular analysis of the genetic material.

2. The method of claim 1 wherein the one or more plant embryos comprise one or more immature plant embryos.

3. The method of claim 1 wherein antimicrobial agents and/or minimal growth media are added to the aqueous solution.

4. The method of claim 1 wherein the one or more plant embryos are stored under dark conditions.

5. The method of claim 1 wherein the one or more plant embryos are stored at approximately 4 degrees Celsius.

6. The method of claim 1 further comprising transferring the one or more plant embryos for continued storage.

7. The method of claim 1 further comprising transferring the one or more plant embryos to a germination medium.

8. The method of claim 1 further comprising germinating at least one of the one or more plant embryos.

9. The method of claim 1 wherein the method of storing is automated.

10. The method of claim 1 wherein said molecular analysis is genotyping.

11. The method of claim 1, further comprising the step of selecting or discarding the plant embryo based on the results of the molecular analysis.

12. The method of claim 1, wherein the plant embryo is washed in the aqueous solution prior to agitation.

* * * * *